United States Patent
Simhadri et al.

(10) Patent No.: US 11,069,036 B1
(45) Date of Patent: Jul. 20, 2021

(54) METHOD AND SYSTEM FOR REAL-TIME AND OFFLINE DE-IDENTIFICATION OF FACIAL REGIONS FROM REGULAR AND OCCLUDED COLOR VIDEO STREAMS OBTAINED DURING DIAGNOSTIC MEDICAL PROCEDURES

(71) Applicant: GE Precision Healthcare LLC, Milwaukee, WI (US)

(72) Inventors: Govindappa Simhadri, Bangalore (IN); Raghu Prasad, Bangalore (IN); Sandeep Lakshmipathy, Bangalore (IN); Jayanth Ganapathiraju, Bangalore (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 13 days.

(21) Appl. No.: 16/733,596

(22) Filed: Jan. 3, 2020

(51) Int. Cl.
- G06K 9/00 (2006.01)
- G06T 5/00 (2006.01)
- G16H 30/40 (2018.01)

(Continued)

(52) U.S. Cl.
CPC .......... *G06T 5/002* (2013.01); *G06K 9/00241* (2013.01); *G06N 20/20* (2019.01);
(Continued)

(58) Field of Classification Search
CPC combination set(s) only.
See application file for complete search history.

(56) References Cited

U.S. PATENT DOCUMENTS

| | | | |
|---|---|---|---|
| 2009/0028432 A1* | 1/2009 | Rossato | G06T 7/194 382/173 |
| 2013/0129234 A1* | 5/2013 | Farid | G06T 7/0002 382/228 |

(Continued)

OTHER PUBLICATIONS

Ning et al., "Spatially Supervised Recurrent Convolutional Neural Networks for Visual Object Tracking," arXiv:1607.05781v1 [cs.CV], Jul. 19, 2016, 10 pages.

(Continued)

*Primary Examiner* — Xin Jia
(74) *Attorney, Agent, or Firm* — Amin, Turocy & Watson, LLP

(57) ABSTRACT

Systems and techniques that facilitate real-time and/or offline de-identification of facial regions from regular and/or occluded color video streams obtained during diagnostic medical procedures are provided. A detection component can generate a bounding box substantially around a person in a frame of a video stream, can generate a heatmap showing key points or anatomical masks of the person based on the bounding box, and can localize a face or facial region of the person based on the key points or anatomical masks. An anonymization component can anonymize pixels in the frame that correspond to the face or facial region. A tracking component can track the face or facial region in a subsequent frame based on a structural similarity index between the frame and the subsequent frame being above a threshold. If the structural similarity index between the frame and the subsequent frame is above the threshold, the tracking component can track the face or facial region in the subsequent frame without having the detection component generate a bounding box or a heatmap in the subsequent frame, and the anonymization component can anonymize pixels in the subsequent frame corresponding to the tracked face or facial region.

20 Claims, 25 Drawing Sheets

(51) Int. Cl.
*G06N 20/20* (2019.01)
*G06T 7/246* (2017.01)
*G16H 30/20* (2018.01)

(52) U.S. Cl.
CPC ............. *G06T 7/248* (2017.01); *G16H 30/40* (2018.01); *G06T 2207/10016* (2013.01); *G06T 2207/20081* (2013.01); *G06T 2207/30201* (2013.01); *G16H 30/20* (2018.01)

(56) References Cited

U.S. PATENT DOCUMENTS

| | | | |
|---|---|---|---|
| 2018/0225517 A1* | 8/2018 | Holzer | G06K 9/22 |
| 2020/0151860 A1* | 5/2020 | Safdarnejad | G06T 7/162 |
| 2021/0019892 A1* | 1/2021 | Zhou | G06K 9/4614 |

OTHER PUBLICATIONS

Zhang et al., "Joint Face Detection and Alignment Using Multitask Cascaded Convolutional Networks," IEEE Signal Processing Letters, vol. 23, No. 10, Oct. 2016, 5 pages.

Ren et al., "Faster R-CNN: Towards Real-Time Object Detection with Region Proposal Networks," arXiv:1506.01497v3 [cs.CV], Jan. 6, 2016, 14 pages.

Liu et al., "SSD: Single Shot MultiBox Detector," arXiv:1512.02325v5 [cs.CV], Dec. 29, 2016, 17 pages.

Held et al., "Learning to Track at 100 FPS with Deep Regression Networks," arXiv:1604.01802v2 [cs.CV], Aug. 16, 2016, 26 pages.

Kalal et al., "Forward-Backward Error: Automatic Detection of Tracking Failures," International Conference on Pattern Recognition, Aug. 23-26, 2010, 4 pages.

\* cited by examiner

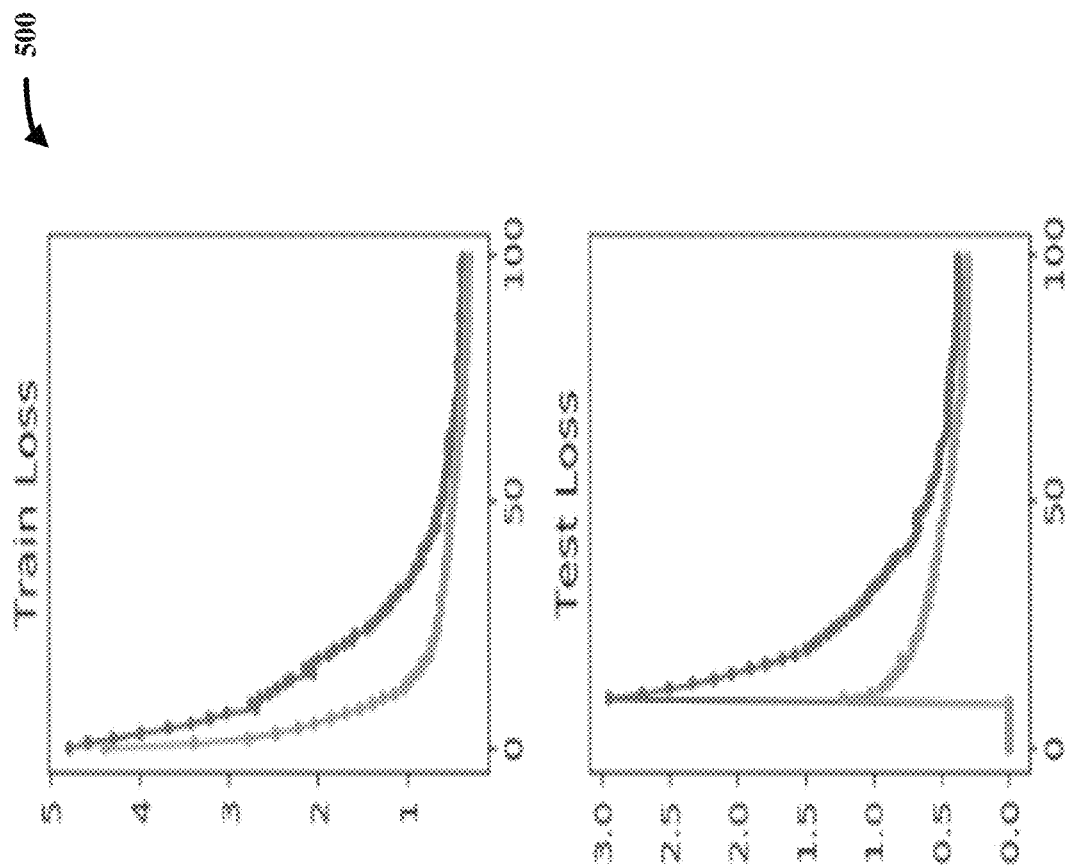
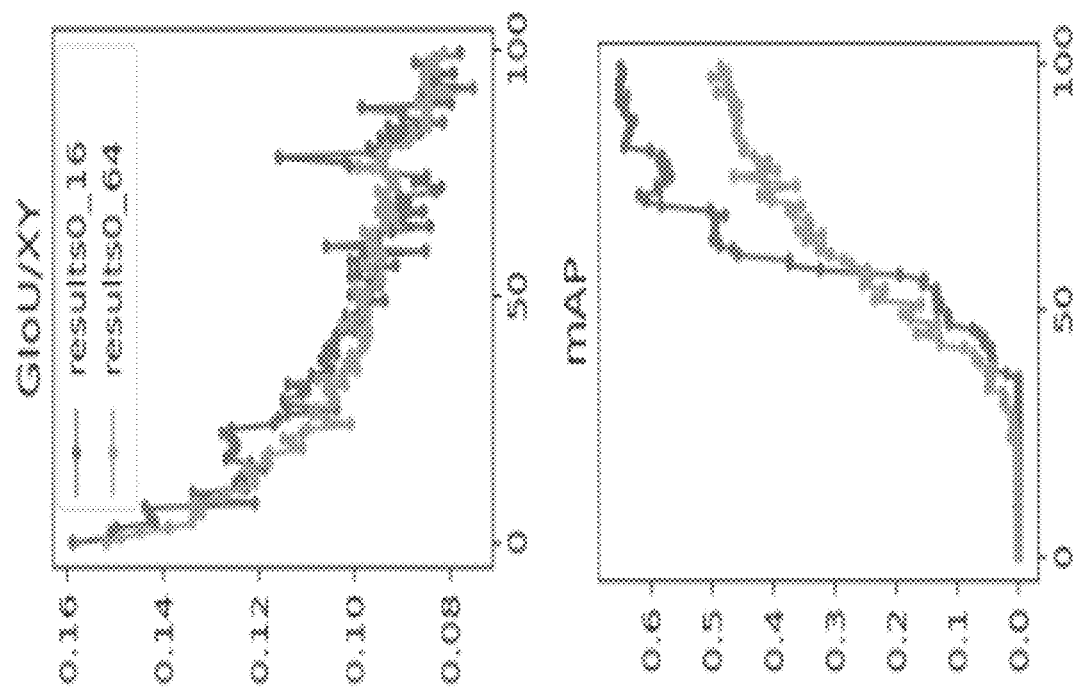
FIG. 5

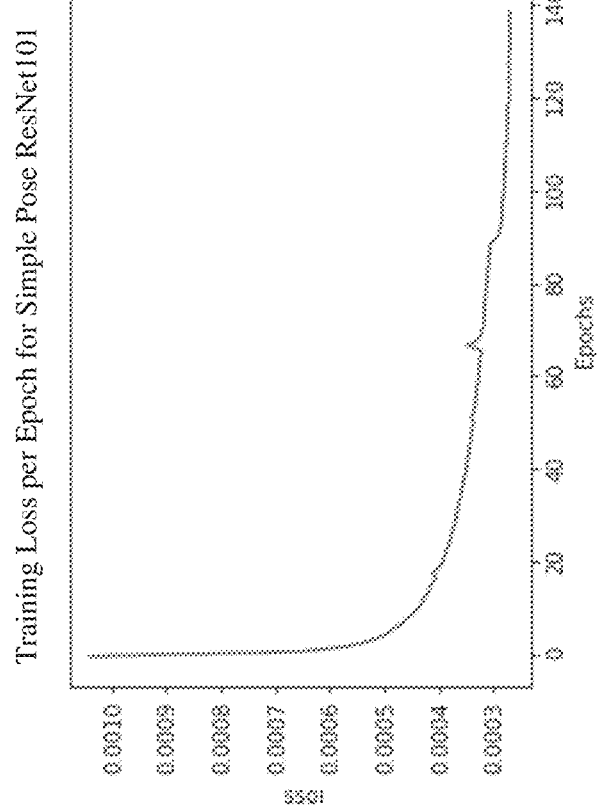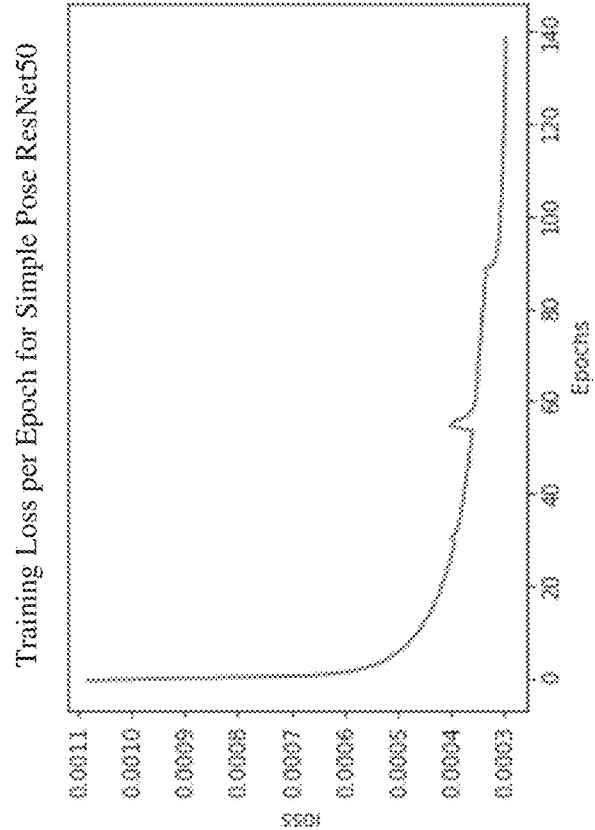
FIG. 8

METHOD AND SYSTEM FOR REAL-TIME AND OFFLINE DE-IDENTIFICATION OF FACIAL REGIONS FROM REGULAR AND OCCLUDED COLOR VIDEO STREAMS OBTAINED DURING DIAGNOSTIC MEDICAL PROCEDURES

BACKGROUND

The subject disclosure relates generally to facial anonymization/de-identification, and more particularly to systems and computer-implemented methods that facilitate automated facial anonymization/de-identification in regular and/or occluded color and/or depth video streams obtained during diagnostic and therapeutic medical procedures.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate real-time and/or offline de-identification of facial regions from regular and/or occluded color and/or depth video streams obtained during diagnostic medical procedures are described. Further, the method and a system can facilitate de-identification of facial regions in anterior-posterior (AP), posterior-anterior (PA), lateral, supine, prone, and all DICOM patient positioning attributes.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise a detection component, which can generate a bounding box substantially around a person in a frame of a video stream. In various aspects, the detection component can generate a heatmap showing key points or anatomical masks of the person based on the bounding box. In various instances, the detection or identification component can localize a face or facial region of the person based on the spherical key points or anatomical masks or mask. In various embodiments, the computer-executable components can comprise an anonymization component, that can anonymize or de-identify pixels in the frame that correspond to the facial region and/or any identifiable features of human body. In various embodiments, the computer-executable components can comprise a tracking component, that can track the face or facial region in a subsequent frame based on a structural similarity index between the frame and the subsequent frame being above a threshold. In one or more embodiments, if the structural similarity index is above the threshold, the tracking component can track the face or facial region in the subsequent frame, the detection component can refrain from generating a bounding box or a heatmap in the subsequent frame, and the anonymization component can anonymize pixels in the subsequent frame corresponding to the face or facial region.

According to one or more embodiments, the above-described system can be implemented as a computer-implemented method.

According to one or more embodiments, the above-described system can be implemented as a computer program product for facilitating automated face or facial region anonymization in video streams, the computer program product comprising a computer readable memory having program instructions embodied therewith, the program instructions executable by a processing component to cause the processing component to perform various acts such as neural network processing, image processing, video processing, tracking, and so on.

DESCRIPTION OF THE DRAWINGS

FIGS. 5-6 illustrate example, non-limiting graphs depicting training results of a bounding box component in a system that facilitates automated facial anonymization/de-identification in regular and/or occluded video streams (e.g., supported RGB, RGBA8, YUYV and all supported color formats) obtained during diagnostic medical procedures in accordance with one or more embodiments described herein.

FIGS. 8-9 illustrate example, non-limiting graphs depicting training results of a heatmap component in a system that facilitates automated facial anonymization/de-identification in regular and/or occluded video streams obtained during diagnostic medical procedures in accordance with one or more embodiments described herein.

DETAILED DESCRIPTION

Figure 1:
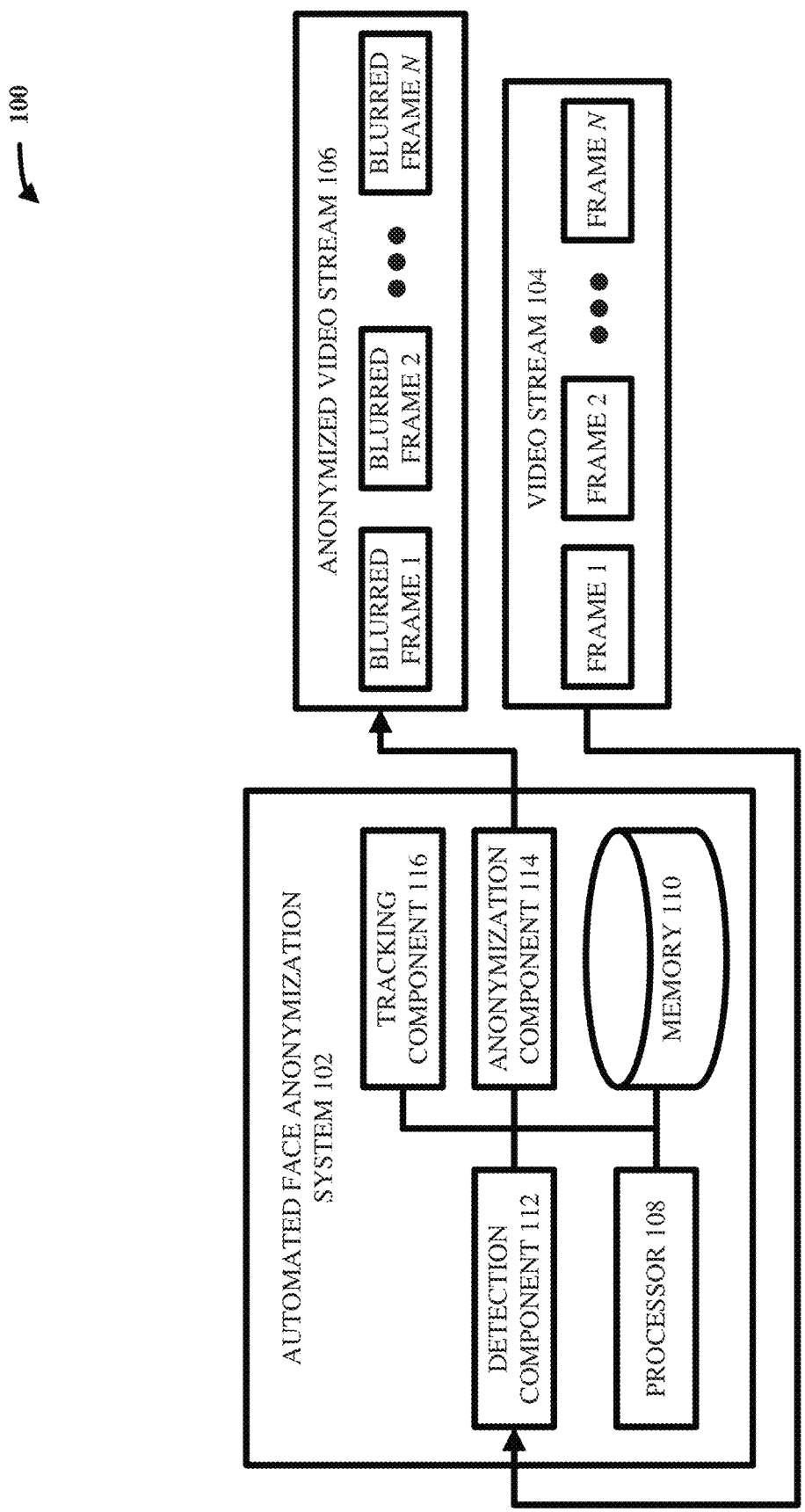
FIG. 1 illustrates a block diagram of an example, non-limiting system that facilitates automated facial anonymization/de-identification in regular and/or occluded video (e.g., supported RGB, RGBA8, YUYV and all supported color formats) streams obtained during diagnostic medical procedures in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Many modern medical diagnostic procedures involve capturing image data (e.g., still images, videos, and so on) of medical patients. Some examples include x-ray scans of patients, computed tomography (CT) scans of patients, magnetic resonance imaging (MRI) scans of patients, positron emission tomography—computed tomography (PET/CT) scans of patients, positron emission tomography—magnetic resonance imaging (PET/MRI) scans of patients, DGS scans of patients, interventional scans of patients, mammography scans of patients, ultrasound scans of patients, images/videos for checking therapy/exercise form and/or posture of patients, images/videos for benchmarking temporal progress of visible symptoms of patients, pre-scan streaming videos/images of patients, and so on. In many cases, this recorded image data can contain rich information that can be used to train machine learning and/or deep learning algorithms employed by medical diagnostic devices (e.g., artificial intelligence systems can be trained via supervised learning on libraries of collected medical images/videos in order to learn how to accurately recognize/diagnose specific diseases based on displayed symptoms, to learn how to accurately generate prognoses for individual patients based on displayed symptoms, to learn how to recommend effective treatments for individual patients based on displayed symptoms, and so on). However, in the interest of protecting patient privacy, many laws and regulations (e.g., HIPAA Act of 1996) permit the use of such captured image data without the express consent of the depicted patients only when pertinent patient identification information in such captured image data is sufficiently anonymized/de-identified (e.g., by blurring, pixelating, removing, or otherwise blocking the face or facial region of a patient depicted in an image or video). Thus, systems and techniques for automatically, effectively, efficiently, and robustly anonymizing face or facial regions in medical image/video data are advantageous.

Existing automated anonymization/de-identification systems and techniques are highly computationally intensive and complex, and they generally use image pyramids to identify face or facial regions at varying scales/sizes. Thus, existing systems/techniques are effective only for anonymizing offline video streams (e.g., pre-recorded and stored videos) and are unsuitable for anonymizing real-time video streams. Moreover, such existing systems/techniques generally fail when at least one of the following occur: sudden changes in illumination conditions, sudden changes in facial orientations, non-frontal facial orientations, partial facial and/or bodily occlusion (e.g., where the face or facial region and/or body of the patient is not fully visible in the image and/or video frame because it is blocked by another object), visibility of background clutter, sudden camera movement, and so on. Existing systems/techniques that are robust enough to avoid failure under the above conditions are generally too computationally intensive and slow to be effectively used for real-time anonymization/de-identification of live video streams when patient is positioned in any suitable orientation, such as anterior-posterior (AP), posterior-anterior (PA), lateral, supine, prone, and/or all DICOM patient positioning attributes.

Therefore, there is a need for anonymization/de-identification algorithms that are robust enough to avoid failure under common conditions (e.g., illumination changes, camera motion, partial occlusion, background clutter, and so on) and that are simultaneously efficient enough to be used for real-time processing of live and/or nearly-live video streams.

Various embodiments of the subject claimed innovation can solve these problems in the prior art. One or more embodiments described herein include systems, computer-implemented methods, apparatus, and/or computer-program products that can facilitate automated facial anonymization/de-identification in regular and/or occluded video streams obtained during diagnostic medical procedures. In various instances, the subject claimed innovation can detect, via a trained object detection algorithm, a person (e.g., a patient, a doctor, a nurse, and so on) in a frame of a video stream (e.g., live and/or pre-recorded) and can generate a bounding box substantially around the person in the frame (e.g., identify coordinates in the frame of a rectangular boundary/area within which all or nearly all of the person is located and outside which the remainder of the frame is located). In some embodiments, the subject claimed innovation can output a confidence value for each bounding box (e.g., between 0 and 1), representing a level of confidence and/or a likelihood that the contents of the bounding box were not misidentified as a person. In various instances, the subject claimed innovation can estimate, via a trained multi-pose estimation algorithm, a pose of the person within the bounding box (e.g., determine/infer how the person's body is physically oriented in the bounding box, such as standing, sitting, bent over, twisting/turning, facing the front of the bounding box, facing the back of the bounding box, facing a side of the bounding box, extending arms and/or legs up, down, or to a side, and so on) and can generate a heatmap showing key points or anatomical masks of the person (e.g., a key point for each shoulder, a key point for each elbow, a key point for each wrist, a key point for each hip, a key point for each knee, a key point for each ankle, a key point for each ear, a key point for each eye, a key point for the nose, a key point for the chin, and so on). Based on the key points or anatomical masks in the heatmap, the subject claimed innovation can localize the face or facial region of the person (e.g., identify coordinates of the key points or anatomical masks which correspond to the eyes, ears, nose, chin, and so on). In various instances, the subject claimed innovation can anonymize pixels in the frame that correspond to the face or facial region of the person (e.g., pixilation, blurring, and/or blocking of pixels that surround the facial key points or anatomical masks). Thus, the face or facial region of the person in the frame can be anonymized/de-identified to prevent visual recognition by an observer of the frame, and the frame can be stored and/or streamed as desired. With sufficient training on appropriate datasets (e.g., COCO dataset), embodiments of the subject claimed innovation can accurately and robustly detect one or more persons in a frame, localize their face or facial regions, and anonymize their face or facial regions in a highly fault tolerant manner, such as even when their face or facial regions and/or bodies are partially occluded (e.g., blocked from view by another object depicted in the frame, such as MRI headgear, patient monitoring devices and/or breathing tubes, medical blankets/bandages, and so on) and/or even if they are not directly facing the camera (e.g., person depicted as facing partially and/or wholly sideways and/or backwards in the frame).

In various embodiments, the subject claimed innovation can receive a subsequent frame in the video stream and can calculate a structural similarity index (e.g., a defined mathematical value that is a function of two images) between the subsequent frame (now the current frame) and the frame (now the previous frame). If the structural similarity index is greater than and/or equal to a threshold value, the subject claimed innovation can, in various embodiments employ an appearance-based tracker to track the face or facial region of the person in the subsequent frame (e.g., to determine new coordinates in the subsequent frame that correspond to the face or facial region of the person, which face or facial region was just detected, localized, and anonymized in the previous frame). In various aspects, such tracking can allow the subject claimed innovation to localize the face or facial region of the person in the subsequent frame without having to analyze the subsequent frame with the trained object detection and multi-pose estimation algorithms. This can, in various instances, conserve time and computing resources, which can allow for a commensurate increase in the streaming rate of anonymized frames.

In other words, embodiments of the subject claimed innovation can employ fault tolerant object detection and pose estimation algorithms (which can, in some cases, be computationally expensive and/or time consuming to run) to localize and anonymize a face or facial region depicted in a first frame. Then, in subsequent frames that are sufficiently structurally similar to the first frame, the subject claimed innovation can employ an appearance-based tracking algorithm (which can be less computationally expensive and/or time consuming to run than the object detection and pose estimation algorithms) to localize and anonymize the face or facial region in the subsequent frames. Overall, this can result in robust and fault tolerant facial anonymization/de-identification at a sufficiently high frame rate so as to be suitable for use in real-time and/or live-streamed videos.

Various embodiments of the subject innovation can be employed to use hardware and/or software to solve problems that are highly technical in nature (e.g., to facilitate automated facial anonymization/de-identification in regular and/or occluded video streams obtained during diagnostic medical procedures.), that are not abstract and that cannot be performed as a set of mental acts by a human. Further, some of the processes performed can be performed by a specialized computer for carrying out defined tasks related to automated facial anonymization/de-identification (e.g., generating a bounding box substantially around a person in a frame of a video stream; generating a heatmap showing key points or anatomical masks of the person based on the bounding box; localizing a face or facial region of the person based on the key points or anatomical masks; anonymizing pixels in the frame that correspond to the face or facial region; tracking the face or facial region in a subsequent frame based on a structural similarity index between the frame and the subsequent frame being above a threshold; and so on). In various aspects, the subject claimed innovation can provide technical improvements to the field of automated facial anonymization/de-identification, by leveraging robust and fault tolerant object detection and pose estimation algorithms to localize and anonymize a face or facial region in a first frame, and by leveraging a fast, appearance-based tracking algorithm to localize and anonymize the face or facial region in a subsequent frame that is sufficient structurally similar to the first frame. Such embodiments can provide accurate, reliable, and efficient facial anonymization in a plurality of frames without having to run computationally expensive object detection and pose estimation algorithms for every frame. Such automated facial anonymization/de-identification systems can thus provide robust and fault tolerant facial anonymization at frame rates high enough to allow processing of real-time and/or near real-time videos, and thus constitutes a concrete and tangible technical improvement in the prior art.

FIG. 1 illustrates a block diagram of an example, non-limiting system 100 that can facilitate automated facial anonymization/de-identification in regular and/or occluded video streams obtained during diagnostic medical procedures in accordance with one or more embodiments described herein. As shown, the automated face anonymization system 102 can, in various embodiments, anonymize face or facial regions in one or more frames (e.g., frame 1, frame 2, . . . , frame n where n can be any suitable positive integer, and so on) of a video stream 104 in order to generate an anonymized video stream 106, which can comprise anonymized/blurred frames (e.g., blurred frame 1, blurred frame 2, . . . , blurred frame n, and so on). In various aspects, the video stream 104 can be any suitable pre-recorded, live-streamed, and/or nearly live-streamed video content (e.g., pre-recorded and/or real-time security camera footage of a hospital or other building; pre-recorded and/or real-time footage of medical diagnostic equipment, such as pre-scan and/or in situ MRI videos, pre-scan and/or in situ CT videos, X-ray, Ultrasound procedure videos, interventional procedure videos, and so on; pre-recorded and/or real-time footage of a mobile device, such as a cell phone; pre-recorded and/or real-time footage of an autonomous and/or remotely-controlled vehicle, such as a drone or self-driving automobile; and so on). In various embodiments, the video stream 104 can be any suitable pre-recorded, real-time, and/or nearly real-time video feed/content which is desired to be anonymized/de-identified. In various embodiments, the anonymized video stream 106 can be generated by the automated face anonymization system 102 in a frame-by-frame fashion (e.g., anonymizing one frame at a time), and can be stored and/or streamed (e.g., in real-time or nearly real-time) as desired.

In various cases, any frame in the video stream 104 that depicts a face or facial region of a person can be anonymized (e.g., one or more face or facial regions in the frame can be pixelated, blurred, blocked, removed, replaced with a mask, and so on), thereby yielding an anonymized and/or blurred frame. For instance, if frame 1 depicts a face or facial region of a person, frame 1 can be anonymized (e.g., the face or facial region in frame 1 can be pixelated) and stored and/or streamed as blurred frame 1. Similarly, frame 2 can be stored and/or streamed as blurred frame 2 after anonymization, frame n can be stored and/or streamed as blurred frame n after anonymization, and so on. In some cases, a frame of the video stream 104 can depict no person at all (e.g., a frame depicting an empty hospital bed, and so on). In such case, no anonymization of the frame is necessary, and so the frame can be stored and/or streamed as is.

In various embodiments, the video stream 104 can include RGB frames (e.g., where each pixel of a frame generates its exhibited color via a combination of red, green, and blue light intensities). In such case, the anonymized video stream 106 can also include RGB frames. In various embodiments, any other suitable type of color frames can be incorporated (e.g., RGBA8, YUV, YUVY, Y16, and so on). In various embodiments, the video stream 104 can include depth frames (e.g., video frames where each pixel exhibits one or more values to denote its overall color as well as a value denoting depth and/or distance away from the camera of the depicted point). In such case, the anonymized video stream 106 can also include depth frames. In other words, various embodiments of the subject claimed innovation can be configured to operate on any suitable color frames, and various embodiments of the subject claimed innovation can be configured to operate on any suitable depth frames.

In various embodiments, the automated face anonymization system 102 can comprise a processor 108 (e.g., computer processing unit, microprocessor, and so on) and a computer-readable memory 110 that is operably and/or operatively and/or communicatively connected/coupled to the processor 108. The memory 110 can store computer-executable instructions which, upon execution by the processor 108, can cause the processor 108 and/or other components of the automated face anonymization system 102 (e.g., detection component 112, anonymization component 114, tracking component 116, and so on) to perform one or more acts. In various embodiments, the memory 110 can store computer-executable components (e.g., detection component 112, anonymization component 114, tracking component 116, and so on), and the processor 108 can execute the computer-executable components.

In various embodiments, the automated face anonymization system 102 can comprise a detection component 112. The detection component 112 can, in various instances, localize a face or facial region of a person in a frame of the video stream 104. In one or more aspects, the detection component 112 can accomplish this localization by detecting a person in the frame via a trained object detection algorithm (e.g., a trained YOLOv3 ("You Only Look Once") neural network algorithm) and estimating a pose of the detected person via a trained multi-pose estimation algorithm (e.g., a trained Simple Pose ResNet (Residual Neural Network) algorithm).

In various instances, the trained object detection algorithm can analyze the frame, detect a person in the frame with a given confidence and/or probability level (e.g., determine with a particular certainty level whether the frame depicts a human being), and generate an appropriately-sized bounding box around and/or substantially around the person (e.g., identify coordinates of a rectangular boundary in the frame with substantially minimized interior area that substantially circumscribes the detected person). In various aspects, the detection component 112 can upscale the bounding box (e.g., enlarge the height and/or enlarge the width of the bounding box) by any suitable predetermined amount and/or proportion to help ensure that the bounding box properly circumscribes the entire person and/or substantially the entire person (e.g., lengthening and/or widening the bounding box by some desired absolute amount and/or some desired percentage in order to help avoid a scenario where portions and/or limbs of the depicted person are outside the bounding box). In various cases, the bounding box can separate the detected person from the rest of the frame, allowing that portion of the frame that is within the bounding box to be analyzed without requiring commensurate analysis of the rest of the frame. With sufficient and/or appropriate training (e.g., supervised learning on suitably broad/rich libraries), the object detection algorithm can enable the detection component 112 to accurately and robustly detect one or more persons depicted in a frame of the video stream 104 even if the person's face or facial region and/or body is partially occluded (e.g., such as by a medical blanket, MRI headset, and so on) and/or even if the person is not in a standard upright posture (e.g., crouched, sitting, lying down, twisting/turning, limbs extending in various directions, and so on).

In various instances, the trained multi-pose estimation algorithm can analyze the bounding box (e.g., analyze that portion of the frame that is within the bounding box) and generate a heatmap of the person. In various cases, the heatmap can show key points or anatomical masks of the person such as primary joints of the person (e.g., shoulders, elbows, wrists, hips, knees, ankles, neck, and/or so on) and primary facial features of the person (e.g., eyes, ears, nose, mouth, chin, and/or so on). In various instances, the heatmap can include an arrangement of vertices corresponding to the key points or anatomical masks and lines connecting the vertices, superimposed over the person in the bounding box such that each vertex is substantially and/or roughly positioned over a key point of the person (e.g., one vertex superimposed over the right shoulder of the person, one vertex superimposed over the left hip of the person, one vertex superimposed over the chin of the person, and/or so on). In various cases, the trained multi-pose estimation algorithm can label one or more key points or anatomical masks and can generate coordinates defining the location of one or more key points or anatomical masks within the frame. In various aspects, the detection component 112 can localize the face or facial region of the person by identifying, from the heatmap, the coordinates of those key points or anatomical masks that correspond to facial features (e.g., ears, eyes, nose, chin, and so on). Note that, in various embodiments, the multi-pose estimation algorithm can enable the detection component 112 to localize the face or facial region and/or head of the detected person even if the face or facial region of the detected person is not clearly depicted in the frame (e.g., partially occluded by a medical apparatus, partially occluded because the person is facing away from the camera, and so on).

With sufficient and/or appropriate training (e.g., supervised learning, unsupervised learning, reinforcement learning, and so on) of the object detection and multi-pose estimation algorithms, the detection component 112 can, in various embodiments, accurately and robustly localize face or facial regions of persons depicted in frames of the video stream 104, even if sudden/rapid camera movements occur, even if sudden illumination changes occur, even if the person's face or facial region and/or body is partially occluded, even if there is considerable background clutter visible in the frame, even if there are non-frontal facial orientations (e.g., tilted heads, turned heads, and so on), and so on.

In various embodiments, after localizing one or more face or facial regions, the detection component 112 can initialize the tracking component 116 (e.g., such that the tracking component 116 is prepared to process a subsequent frame).

In one or more embodiments, the automated face anonymization system 102 can comprise an anonymization component 114. The anonymization component 114 can, in various instances, anonymize the localized face or facial regions of the detected persons. In various embodiments, the anonymization component 114 can identify pixels corresponding to and/or surrounding the facial key points or anatomical masks of a detected person (e.g., identifying pixels that are within a desired and/or predetermined radius of the facial key points or anatomical masks, identifying pixels that are within any other suitably-shaped and desired/predetermined distance/dimensions of the facial key points or anatomical masks, and so on). In various aspects, the anonymization component 114 can facilitate anonymization of the identified pixels by pixilating the pixels surrounding the facial key points or anatomical masks, by performing gaussian blurring of the pixels surrounding the facial key points or anatomical masks, by setting to zero (and/or any other desired and/or predetermined number) the color values of the pixels surrounding the facial key points or anatomical masks, by randomizing the color values of the pixels surrounding the facial key points or anatomical masks, by replacing such pixels with a mask, and so on. In various instances, the result can be that the face or facial region of the detected person is no longer visually recognizable in the frame (e.g., in the blurred frame). The anonymized/blurred frame can then be stored and/or streamed as desired.

In various aspects, the anonymization component 114 can refrain from anonymizing pixels that are determined to correspond to and/or surround facial key points or anatomical masks when the multi-pose estimation algorithm determines that the facial key points or anatomical masks are not visible in the frame (e.g., because the person's pose/posture indicates that the person is facing away from the camera and/or that the face or facial region is already occluded by some other object depicted in the frame). For instance, if the person is standing with their right side facing the camera and their right arm extending upward such that their right arm occludes a portion of their face or facial region, the multi-pose estimation algorithm can determine such posture and the anonymization component 114 can accordingly pixilate only those portions of the person's face or facial region that are not occluded by the person's right arm. In various embodiments, all pixels corresponding to the facial key points or anatomical masks can be anonymized even if the face or facial region is already partially occluded in the frame.

In various embodiments, the automated face anonymization system 102 can comprise a tracking component 116. In various aspects, if tracking has been initialized (e.g. by the detection component 112), the tracking component 116 can compute a structural similarity index (SSIM) between a subsequent frame and the frame that was just previously anonymized. In various cases, the SSIM can be a scalar based on one or more pixel values and/or functions of pixel values of two separate frames in the video stream 104, where the SSIM measures and/or quantifies a level of similarity between the two frames (e.g., similarity value between 0 and 1, with higher values indicating more similarity; similarity value between −1 and 1, with higher values indicating more similarity; and so on). In various embodiments, any other suitable mathematical measure of similarity between two images can be implemented. In one or more embodiments, the tracking component 116 can determine whether the SSIM is greater than and/or equal to a desired and/or predetermined threshold (e.g., 0.8). If this condition is met, the two frames can be considered as sufficiently similar (e.g., sufficiently similar illumination conditions, sufficiently similar depicted object positions/orientations, and so on, as defined by the threshold). If the condition is satisfied, the tracking component 116 can, in various instances, employ one or more trained object tracking algorithms (e.g., Median Flow trackers, GOTURN trackers, any other suitable appearance-based tracking algorithm, and so on) to track and localize the one or more face or facial regions that were detected, localized, and anonymized in the preceding frame (e.g., the one or more face or facial regions that were localized via the object detection and pose-estimation algorithms). The anonymization component 114 can then, in various cases, anonymize the tracked face or facial regions in the now-current frame.

In various embodiments, the trained object tracking algorithms of the tracking component 116 can exhibit a shorter run-time and/or can be less computationally intensive than can the trained object detection and multi-pose estimation algorithms of the detection component 112. Moreover, the trained object tracking algorithms can exhibit comparable accuracy as the trained object detection and multi-pose estimation algorithms when the tracked frame is sufficiently structurally similar to the previously anonymized frame. For instance, the run-time and/or the computer-resource utilization of a Median Flow tracker can be less than the combined run-time and/or the combined computer-resource utilization of a YOLOv3 algorithm and a Simple Pose ResNet algorithm, and yet the Median Flow tracker can localize face or facial regions with comparable and/or acceptable accuracy as the YOLOv3 and Simple Pose ResNet algorithms, provided that the structural similarity between the current frame and the immediately preceding, anonymized frame is sufficiently high (e.g., meeting the desired threshold). Similarly, in various embodiments, the run-time and/or the computer-resource utilization of a GOTURN tracker can be less than the combined run-time and/or the combined computer-resource utilization of a YOLOv3 algorithm and a Simple Pose ResNet algorithm, and yet the GOTURN tracker can localize face or facial regions with sufficiently comparable and/or acceptable accuracy as the YOLOv3 and Simple Pose ResNet algorithms, provided that the structural similarity between the current frame and the immediately preceding, anonymized frame is sufficiently high (e.g., meeting the desired threshold).

Thus, the automated face anonymization system 102 can, in various embodiments, leverage the detection component 112 (which can be considered as more time consuming and/or more computation intensive) to localize face or facial regions in unfamiliar frames (e.g., a frame that is not sufficiently similar to the previous, anonymized frame) and can leverage the tracking component 116 (which can be considered as less time consuming and/or less computation intensive) to localize face or facial regions in familiar frames (e.g., a frame that is sufficiently similar to the previous, anonymized frame).

Such embodiments can perform robust and reliable facial anonymization/de-identification at faster speeds/frame rates than can a system that runs object detection and multi-pose estimation algorithms on every frame. In other words, various embodiments of the subject claimed innovation can perform the more intensive and/or more time consuming computing (e.g., object detection and pose estimation) when analyzing the first frame of the video stream 104, can perform the less intensive and/or less time consuming computing (e.g., object tracking) when analyzing any familiar frame (e.g., a frame that is sufficiently similar to the previous, anonymized frame), and can revert back to the more intensive and/or more time consuming computing (e.g. object detection and pose estimation) when analyzing any unfamiliar frame (e.g., a frame that is not sufficiently similar to the previous anonymized frame). That is, embodiments of the subject claimed innovation can save resources and increase frame rates by employing object detection and pose estimation only when needed (e.g., for unfamiliar frames), rather than employing such algorithms for every frame. Such embodiments can provide acceptable anonymization accuracy while simultaneously saving time and resources, thereby increasing operation speed and enabling processing of real-time and/or near real-time video streams, which is a tangible improvement over systems that perform costly and time-consuming object detection and pose estimation on every single frame of a video stream.

In various cases, the threshold that defines sufficient structural similarity can be set at any suitable and/or desired level (e.g., any value between 0 and 1, any value between −1 and 1, and so on). For example, a higher threshold can result in higher tracking accuracy (e.g., tracking algorithm can be less likely to mis-localize a face or facial region in the frame because it is processing a frame that is more similar to the previous, anonymized frame) at the expense of resulting in lower overall frame rate (e.g., since the threshold is higher, fewer frames will meet the threshold, and so the time-saving tracking algorithm will be run fewer times than if the threshold were lower and the time-consuming detection and pose estimation algorithms will be run more times than if the threshold were lower). As another example, a lower threshold can result in lower tracking accuracy (e.g., the tracking algorithm can be more likely to mis-localize a face or facial region because it is processing a frame that is less similar than the previous, anonymized frame) with the benefit of resulting in higher overall frame rate (e.g., since the threshold is lower, more frames will meet the threshold, and so the time-saving tracking algorithm will be run more times than if the threshold were higher and the time-consuming detection and pose estimation algorithms will be run fewer times than if the threshold were higher). In various embodiments, experiments performed by the inventors of the subject claimed innovation indicate that a threshold level of 0.8 can provide an acceptable balance of tracking accuracy and speed/frame rate. In various embodiments, however, any suitable value can be chosen and can depend on operating context, on operator risk aversion, and so on.

To help clarify the above subject matter, consider the following non-limiting, exemplary illustration. Suppose that the video stream 104 is real-time video content from a hospital room camera that monitors sleeping patients for their safety. The automated face anonymization system 102 can extract (e.g., via an extraction component, not depicted in the FIGs.) a first frame from the video stream 104. The detection component 112 can analyze the first frame with one or more trained object detection algorithms (e.g., YOLOv3) in order to detect a person in the first frame. The trained object detection algorithm can determine that the first frame depicts a patient lying in a hospital bed with a blanket covering a portion of their body. Thus, the object detection algorithm can generate a bounding box in the first frame substantially around the patient, such that all and/or most of the patient's body is circumscribed by the bounding box. In some cases, the object detection algorithm can output a confidence level and/or a probability level that indicates the likelihood that a person was not mistakenly detected. In some cases, the object detection algorithm can upscale a length and/or width of the bounding box to help ensure that all of the patient's body is within the bounding box. The detection component 112 can then, via one or more trained multi-pose estimation algorithms (e.g., Simple Pose ResNet), analyze the bounding box (e.g., the portion of the first frame within the bounding box) and generate a heatmap that identifies the key points or anatomical masks (e.g., joints, face or facial region, and so on) of the detected patient. The key points or anatomical masks can indicate that the ears, eyes, nose, and/or chin of the patient are approximately located at and/or around position (x,y) in the frame. In various cases, the detection component 112 can initialize tracking, based on detecting the patient. In various instances, the anonymization component 114 can pixilate and/or blur those pixels that correspond to and/or surround the face or facial region of the patient (e.g., pixels surrounding location (x,y) in the first frame). The first frame (e.g., first anonymized/blurred frame) can then be stored and/or streamed as desired.

Next, the automated face anonymization component 102 can extract a second frame from the video stream 104. Suppose that this second frame depicts the patient as still lying in the hospital bed with only minor re-adjustment to their position in the hospital bed (e.g., the patient readjusted their head on the pillow, repositioned their arm from their side to above their head, and so on). In such case, since tracking was initialized by the detection component 112, the tracking component 116 can compute an SSIM between the second frame (e.g., the now-current frame) and the first frame (e.g., the immediately-previous, anonymized frame). Since the patient only minorly readjusted their position, the SSIM can be above the predetermined threshold value, which can indicate that the first frame and the second frame are sufficiently structurally similar. In such case, the tracking component 116 can employ one or more trained object tracking algorithms (e.g., Median Flow trackers, GOTURN trackers, and so on) to track the face or facial region of the patient (e.g., to determine that the visible features that were identified as the patient's face or facial region in the first frame moved from location (x,y) to location (x+a, y+b). The anonymization component 114 can anonymize the patient's face or facial region in the second frame (e.g., pixilate and/or blur the pixels corresponding to and/or surrounding location (x+a, y+b) in the second frame). Note that the second frame was anonymized without having to run the object detection and multi-pose estimation algorithms on the second frame. Instead, the less time-consuming and less computation-intensive tracking algorithm was run.

Next, the automated face anonymization component 102 can extract a third frame from the video stream 104. Suppose that this third frame was taken when a nurse walked into the room and flipped on a light switch, such that the third frame is much brighter than the previous frames. In such case, since tracking was still initialized, the tracking component 116 can compute an SSIM between the third frame (the now-current frame) and the second frame (e.g., the immediately-previous, anonymized frame). Since the lights were abruptly/suddenly switched on and a new person walked into the room, the SSIM can be below the predetermined threshold value (e.g., insufficient structural similarity due to sudden illumination change and/or additional person in the room). In such case, the tracking component 116 can reset tracking (e.g., de-initialize tracking), and the automated face anonymization system 102 can analyze the third frame via the detection component 112 rather than the tracking component 116. As explained above, the detection component 112 can determine that the third frame depicts two persons (e.g., the patient and the nurse). Accordingly, two bounding boxes and two heatmaps can be generated (e.g., one each for the patient in the third frame, and one each for the nurse in the third frame), and the anonymization component 114 can anonymize both face or facial regions. The detection component 112 can then re-initialize tracking, and the automated face anonymization system 102 can extract a fourth frame for processing.

In various embodiments, the automated face anonymization system 102 can perform anonymization/de-identification on a patient in any suitable DICOM position/orientation, such as anterior-posterior (AP), posterior-anterior (PA), lateral, supine, prone, and so on. In various embodiments, the automated face anonymization system 102 can perform anonymization/de-identification on any suitable, desired, and/or specified anatomical region of interest that can be set/selected by an operator/technologist (e.g., the subject claimed innovation can be implemented to anonymize regions other than face or facial regions filmed during diagnostic/therapeutic medical procedures, such as other identifiable body characteristics, clothing logos/messages, and so on).

Figure 2:
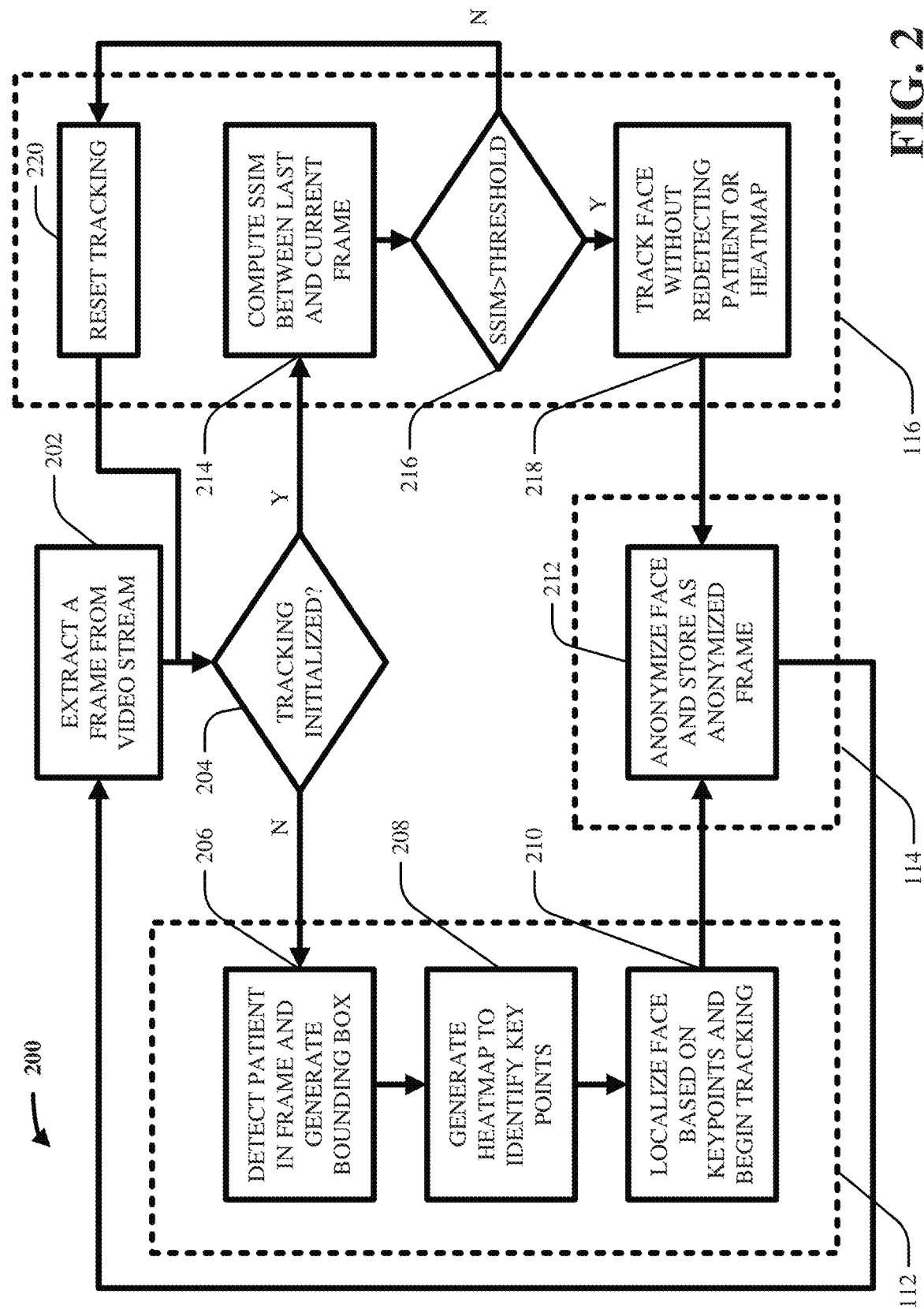
FIG. 2 illustrates a high-level flow diagram of an example, non-limiting computer-implemented method that facilitates automated facial anonymization/de-identification in regular and/or occluded video streams (e.g., supported RGB, RGBA8, YUYV and all supported color formats) obtained during diagnostic medical procedures in accordance with one or more embodiments described herein.

FIG. 2 illustrates a high-level flow diagram of an example, non-limiting computer-implemented method 200 that can facilitate automated facial anonymization/de-identification in regular and/or occluded video streams obtained during diagnostic medical procedures in accordance with one or more embodiments described herein. In various embodiments, the computer-implemented method 200 can be performed by the system 100.

In one or more embodiments, act 202 can include extracting, by a device operatively coupled to a processor, a frame (e.g., frame 1) from a video stream (e.g., video stream 104).

In one or more instances, act 204 can include determining, by the device, whether tracking has been initialized. If tracking is initialized, the computer-implemented method 200 can proceed to act 214. If not, the computer-implemented method 200 can proceed to act 206. For the first frame in a video stream, tracking can be uninitialized by default.

In one or more aspects, act 206 can include detecting, by the device, a patient in the frame and generating a bounding box around the patient (e.g., by the trained object detection algorithm of the detection component 112).

In one or more embodiments, act 208 can include generating a heatmap based on the bounding box to identify key points or anatomical masks of the detected patient (e.g., by the trained multi-pose estimation algorithm of the detection component 112).

In one or more instances, act 210 can include localizing, by the device, a face or facial region of the patient based on the key points or anatomical masks in the heatmap, and tracking can be begun and/or initialized by the device.

In one or more aspects, act 212 can include anonymizing, by the device, the face or facial region of the patient (e.g., via pixilation, blurring, and so on) and storing (and/or streaming, as desired), by the device, the anonymized frame (e.g., anonymizing frame 1 and storing/streaming it as blurred frame 1).

In one or more embodiments, the computer-implemented method 200 can return to act 202 to extract another frame (e.g., frame 2) from the video stream.

In one or more instances, act 204 can include determining, by the device, whether tracking has been initialized. Since tracking was initialized at act 210 during processing of the previous frame (e.g., frame 1), the computer-implemented method 200 can proceed to act 214 with respect to the now-current frame (e.g., frame 2).

In one or more aspects, act 214 can include computing, by the device, an SSIM (e.g., structural similarity index) between the previous, anonymized frame (e.g., frame 1) and the current frame (e.g., frame 2).

In one or more embodiments, act 216 can include determining, by the device, whether the SSIM is greater than and/or equal to a predetermined threshold. If so, the computer-implemented method 200 can proceed to act 218. If not, the computer-implemented method 200 can proceed to act 220.

In various instances, act 218 can include tracking, by the device, the face or facial region of the patient without redetecting the patient or the heatmap (e.g., by using the trained object tracking algorithm of the tracking component 116 and not the object detection and/or multi-pose estimation algorithms of the detection component 112). The computer-implemented method 200 can then proceed to act 212, as described above.

In various instances, act 220 can include resetting, by the device, tracking such that tracking is once again uninitialized. Moreover, the computer-implemented method 200 can then proceed to act 204, as described above.

As shown in FIG. 2, in various embodiments, acts 206-210 can be facilitated by the detection component 112, act 212 can be facilitated by the anonymization component 114, and acts 214-220 can be facilitated by the tracking component 116.

Figure 3:
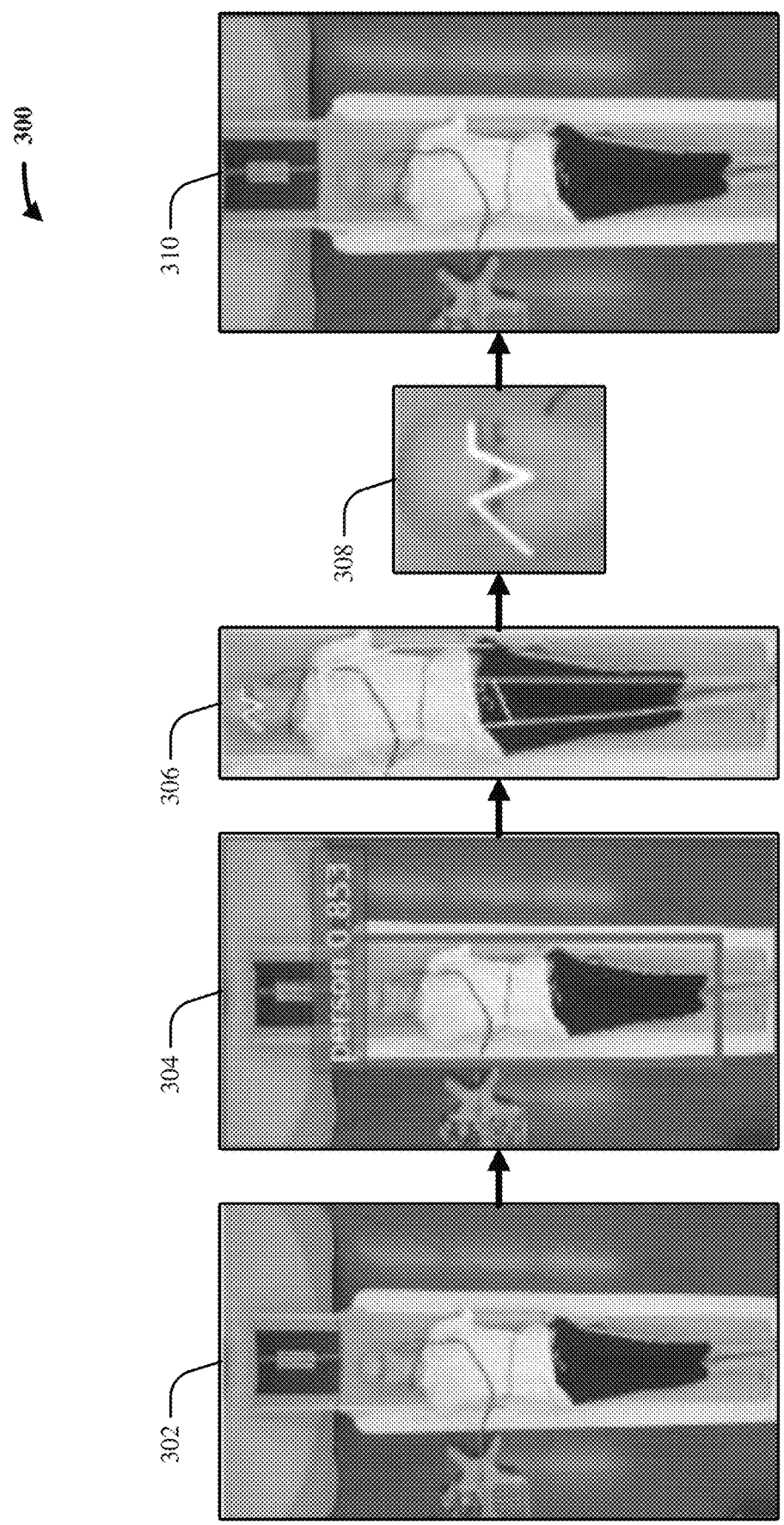
FIG. 3 illustrates example, non-limiting images and/or partial images of a video stream analyzed and/or outputted by a system that facilitates automated facial anonymization/de-identification in regular and/or occluded video streams (e.g., supported RGB, RGBA8, YUYV and all supported color formats) obtained during diagnostic medical procedures in accordance with one or more embodiments described herein.

FIG. 3 illustrates example, non-limiting images and/or partial images 300 of a video stream analyzed and/or outputted by a system that can facilitate automated facial anonymization/de-identification in regular and/or occluded video streams obtained during diagnostic medical procedures in accordance with one or more embodiments described herein. In various embodiments, the images and/or partial images 300 can be processed and/or outputted by the system 100 and/or the computer-implemented method 200.

As shown, a frame 302 can depict a person (e.g., in this case, a medical dummy) lying on a hospital bed, operating table, gurney, and so on. The frame 302 can be extracted from the video stream 104 by the automated face anonymization system 102 for processing. As explained above, the detection component 112 can, via a trained object detection algorithm, detect a person in the frame 302 and generate a bounding box substantially around the person, which can separate the detected person from the background in the frame.

The frame 304 can, in various embodiments, depict the result generated by the object detection algorithm. As shown in the frame 304, a bounding box has been superimposed over the frame such that it has substantially minimal interior area while nevertheless substantially circumscribing the body of the medical dummy. As shown in the frame 304, the bounding box does not completely circumscribe the medical dummy (e.g., the feet of the medical dummy lie outside the bounding box). Nevertheless, the bounding box can still be said to substantially circumscribe the medical dummy because absolute circumscription can, is various instances, be unnecessary. In various embodiments, a bounding box can be said to substantially circumscribe a detected person even though not every square inch of the detected person is within the bounding box, as long as primary portions of the person's body are within the bounding box (e.g., most of the torso within the bounding box, most of the head within the bounding box, and so on).

As shown in the frame 304, the trained object detection algorithm can output a confidence score and/or a probability level associated with the bounding box (e.g., a number between 0 and 1, with higher values corresponding to a higher confidence and/or a higher likelihood that the contents of the bounding box were not misidentified as a person). In the example shown, the object detection algorithm outputted a value of 0.853. In some embodiments, this can indicate the probability/likelihood that misidentification did not occur (e.g., 85.3% sure that a person is depicted within the bounding box, 85.3% chance that a mistaken detection was not made, and so on).

The image 306 can, in various embodiments, depict the result generated by the multi-pose estimation algorithm. As shown in the image 306, the multi-pose estimation algorithm analyzed that portion of the frame 304 that was within the bounding box and generated, based on that analysis, a heatmap showing key points or anatomical masks (e.g., primary joints, primary facial features, and so on) of the medical dummy. As shown, the heatmap can be an arrangement of vertices corresponding to key points or anatomical masks of the medical dummy and lines connecting the vertices. In various embodiments, the heatmap can be superimposed over the medical dummy (e.g., as shown in the image 306, the darker lines and darker vertices are rendered/displayed over the medical dummy). As shown, one vertex (e.g., also referred to as a key point) can be rendered over, substantially over, and/or near the right shoulder of the medical dummy; another vertex can be rendered over, substantially over, and/or near the left shoulder of the medical dummy; a different vertex can be rendered over, substantially over, and/or near the right hip of the medical dummy; a still different vertex can be rendered over, substantially over, and/or near the left hip of the medical dummy; yet another vertex can be rendered over, substantially over, and/or near the left elbow of the medical dummy; and so on. In various embodiments, the trained multi-pose estimation algorithm can place the vertices in locations and/or at coordinates within the frame that it determines and/or infers correspond to key points or anatomical masks of the medical dummy. In other words, the heatmap can represent the multi-pose estimation algorithm's guess as to the various locations and orientations of the medical dummy's primary joints and primary facial features. In one or more embodiments, various key points or anatomical masks in the heatmap can correspond to a facial region of the medical dummy (e.g., the lighter vertices and lighter lines in the image 306 can correspond to the eyes, ears, and nose of the medical dummy).

In various embodiments, the heatmap can visually display an arrangement of key points or anatomical masks/vertices, which arrangement can indicate and/or suggest the pose, posture, and/or bodily orientation of the medical dummy. In various embodiments, the trained multi-pose estimation algorithm can infer one or more locations of facial key points or anatomical masks based on a pose of the detected person (e.g., based on the locations and/or orientations of the key points or anatomical masks corresponding to shoulders, hips, knees, elbows, wrists, and so on). Thus, even if the face or facial region of the medical dummy were not fully visible in the bounding box, the multi-pose estimation algorithm could, in various instances, infer the general location of the face or facial region of the medical dummy based on the key points or anatomical masks that are visible in the bounding box (e.g., based on the primary joints in the bounding box that are not occluded).

The image 308 is a close-up and/or zoomed-in view of the facial key points or anatomical masks of the medical dummy that are displayed in the image 306. In various instances, this can represent the localization and/or extraction of the face or facial region/facial region of the medical dummy based on the heatmap (e.g., identifying which key points or anatomical masks in the heatmap are labeled as facial key points or anatomical masks). As shown in the image 308, the facial key points or anatomical masks can include a key point corresponding to an approximate location of the nose of the medical dummy, two key points or anatomical masks corresponding to approximate locations of the eyes of the medical dummy, two key points or anatomical masks corresponding to approximate locations of the ears of the medical dummy, and so on.

As shown in frame 310, the pixels that are located near and/or that surround the facial key points or anatomical masks of the medical dummy can be anonymized (e.g., via pixilation, blurring, replacement with a mask, and so on). As shown in FIG. 3, the facial details of the medical dummy are more clearly visible in the frame 302 than they are in the frame 310, due to the anonymization. The frame 310 can, in various instances, be stored and/or streamed as desired as the anonymized version of frame 302.

It should be noted that FIG. 3 is exemplary and non-limiting only.

Figure 4:
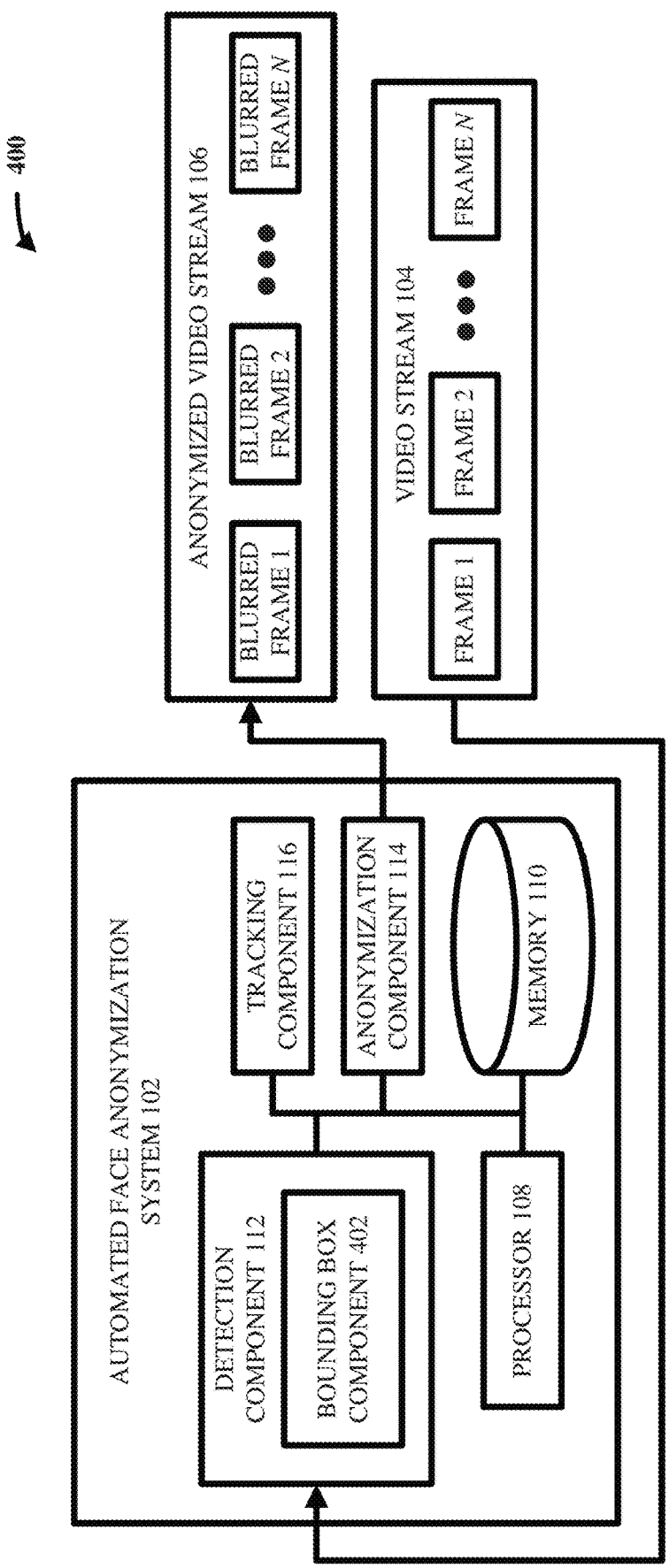
FIG. 4 illustrates a block diagram of an example, non-limiting system including a bounding box component that facilitates automated facial anonymization/de-identification in regular and/or occluded video streams (e.g., supported RGB, RGBA8, YUYV and all supported color formats) obtained during diagnostic medical procedures in accordance with one or more embodiments described herein.

FIG. 4 illustrates a block diagram of an example, non-limiting system 400 including a bounding box component that can facilitate automated facial anonymization/de-identification in regular and/or occluded video streams obtained during diagnostic medical procedures in accordance with one or more embodiments described herein. As shown, the system 400 can, in various embodiments, comprise the same components as the system 100, and can further comprise a bounding box component 402.

In various embodiments, the bounding box component 402 can employ a first machine learning and/or deep learning algorithm that can detect a person within a frame of the video stream 104 and that can accordingly generate a bounding box around each detected person in the frame. In various aspects, each bounding box can have an associated confidence score (e.g., a value between 0 and 1, which indicates a level of confidence that the contents of the bounding box were not misidentified as a person). In various instances, a generated bounding box can be discarded if its associated confidence score falls below a predetermined threshold. In various embodiments, the inventors of the subject claimed innovation found that a confidence threshold of 0.6 can account for tiny and/or blurred face or facial regions depicted in frames. In various aspects, any other suitable confidence threshold can be implemented depending on operational context.

In various embodiments, the first machine learning and/or deep learning algorithm can include any suitable mathematical, statistical, and/or computational technique that can be trained (e.g., via supervised learning) to recognize and/or classify patterns depicted in images (e.g., to recognize when a person and/or another humanoid shape is depicted in a frame of the video stream 104). In various embodiments, a first machine learning and/or deep learning algorithm can comprise one or more linear classifiers (e.g., generative classifiers such as Naïve Bayes, linear discriminant analysis, and so on; discriminative classifiers such as logistic regression, perceptron, support vector machines, and so on; linear affine transformations optimized to achieve global minima; and so on). In various embodiments, a first machine learning and/or deep learning algorithm can comprise one or more non-linear classifiers (e.g., artificial neural networks, non-linear and/or high dimensional support vector machines, and so on). As mentioned above, the first machine learning and/or deep learning algorithm can, in various embodiments, comprise a YOLOv3 object detection algorithm, which is a type of neural network designed to visually recognize semantic classes of objects (e.g., a person) depicted in images. In various embodiments, the YOLOv3 object detection algorithm can be trained on a COCO dataset (e.g., a large-scale object detection, segmentation, and/or captioning library) to learn how to accurately detect a person and/or a humanoid shape in a frame/image (e.g., in a color frame and/or a depth frame). In various embodiments, a pre-trained (GluonCV) mobilenet YOLO v3 algorithm can be implemented as the first machine learning and/or deep learning algorithm. In various aspects, a YOLOv3 algorithm can be fed input images to predict 3D tensors that correspond to three size scales (e.g., a first scale for detecting small objects/face or facial regions, a second scale for detecting medium objects/face or facial regions, and a third scale for detecting large objects/face or facial regions). In such embodiments, image pyramids are not required in order to detect objects on varying size scales, unlike existing facial anonymization techniques which generally rely on computationally intensive image pyramids.

To facilitate some of the above-described machine learning aspects of various embodiments of the subject claimed innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute, and so on) of the present innovation, components of the present innovation can examine the entirety or a subset of the data to which it is granted access and can provide for reasoning about or determine states of the system, environment, and so on from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, z=(z1, z2, z3, z4, zn), to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 6:
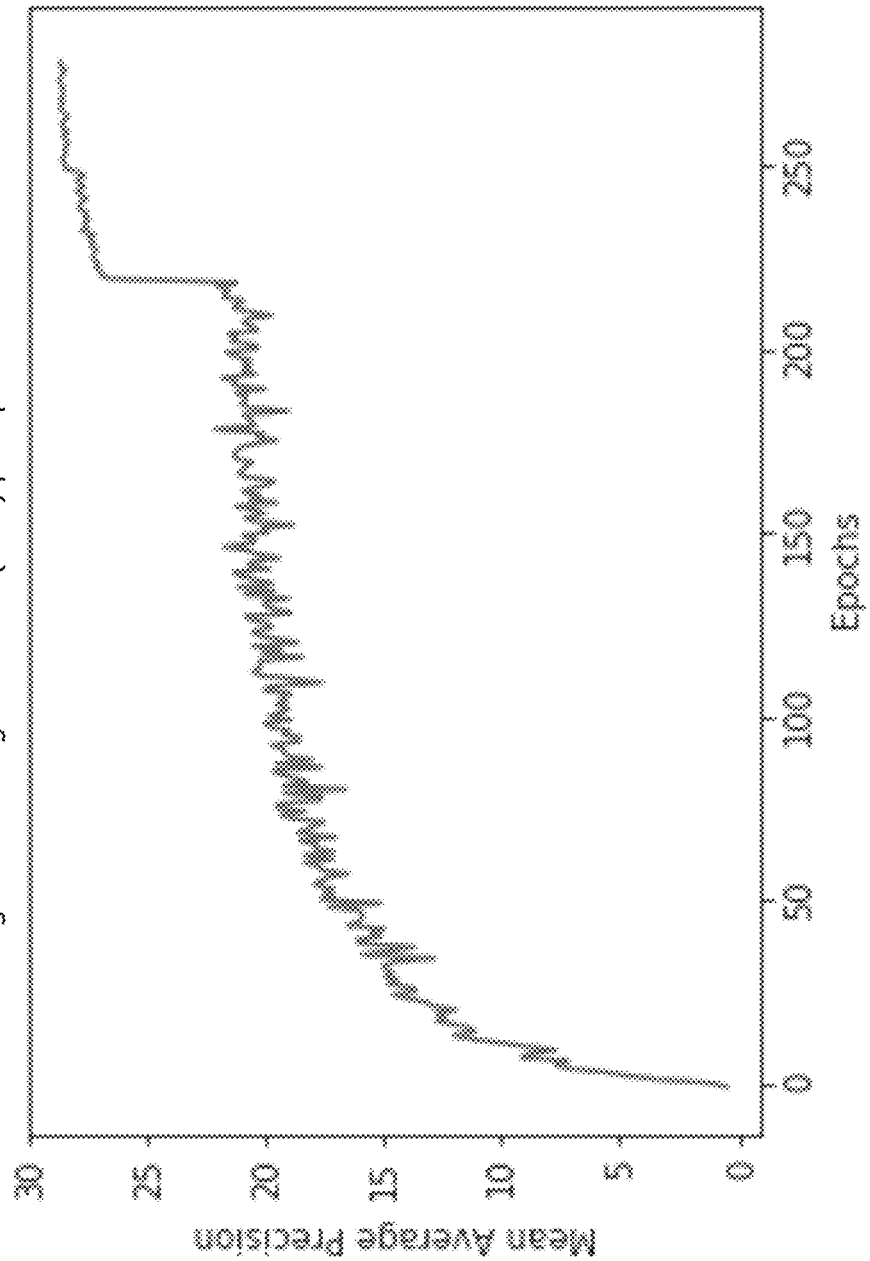

FIGS. 5-6 illustrate example, non-limiting graphs 500 and 600 depicting training results of a bounding box component including a trained YOLOv3 object detection algorithm in a system that can facilitate automated facial anonymization/de-identification in regular and/or occluded video streams obtained during diagnostic medical procedures in accordance with one or more embodiments described herein.

As shown, the graphs 500 depict GIoU/XY, Train Loss, Mean Average Precision (mAP), and Test Loss of a YOLOv3 algorithm trained on a COCO dataset by the inventors of the subject claimed innovation. The COCO dataset can contain multiple subsets of data. As shown in the graphs 500, at least two subsets of data from the COCO dataset were used to train a YOLOv3 algorithm to detect persons in context: the results0_16 data and the results0_64 data. In various instances, the mAP score on the results0_64 data was about 28.5% (0.285) at IoU (intersection over union) thresholds from 0.5 to 0.95 measured in steps of 0.05 for the trained YOLOv3 algorithm at all the size scales (e.g., small, medium, and large). In various instances, the mAP score on the results0_64 data was about 48.7% (0.487) at an IoU threshold of 0.5 for the trained YOLOv3 algorithm at all the size scales. In various aspects, the mAP score on the results0_64 data was about 29.7% (0.297) at an IoU threshold of 0.75 for the trained YOLOv3 algorithm at all the size scales. In various instances, the mAP score on the results0_64 data was about 12.7% (0.127) at IoU thresholds of 0.5 to 0.95 for the trained YOLOv3 algorithm at the small size scale. In various aspects, the mAP score for the results0_64 data was about 29.9% (0.299) at IoU thresholds of 0.5 to 0.95 for the trained YOLOv3 algorithm at the medium size scale. In various instances, the mAP score for the results0_64 data was about 42.3% (0.423) at IoU thresholds of 0.5 to 0.95 for the trained YOLOv3 algorithm at the large size scale.

As shown, graph 600 depicts another measure of mAP for the YOLOv3 algorithm trained on a COCO dataset per epoch.

Figure 7:
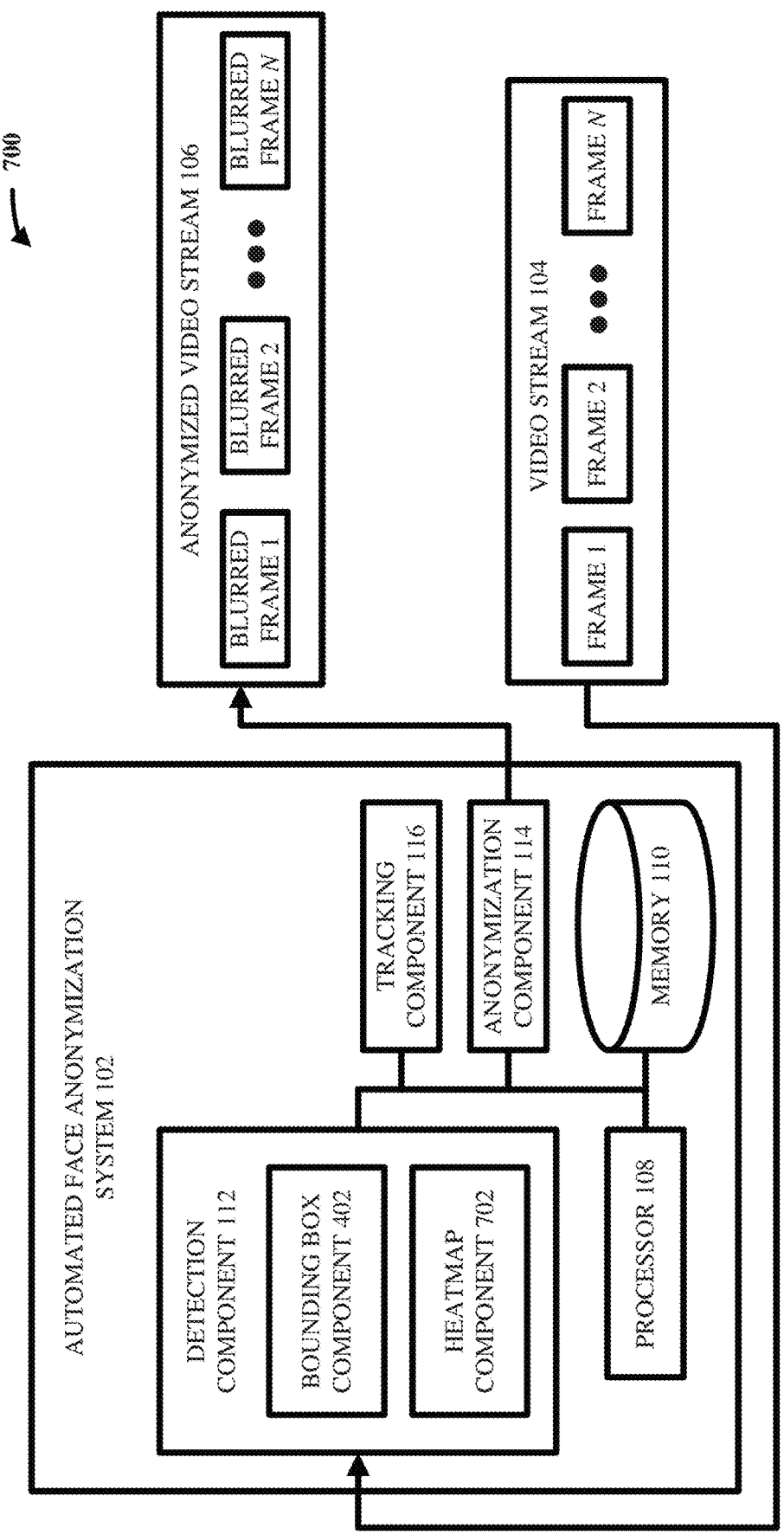
FIG. 7 illustrates a block diagram of an example, non-limiting system including a heatmap component that facilitates automated facial anonymization/de-identification in regular and/or occluded color video streams (e.g., RGB, RGBA8, YUYV and all supported color formats) obtained during diagnostic medical procedures in accordance with one or more embodiments described herein.

FIG. 7 illustrates a block diagram of an example, non-limiting system 700 including a heatmap component that can facilitate automated facial anonymization/de-identification in regular and/or occluded video streams obtained during diagnostic medical procedures in accordance with one or more embodiments described herein. As shown, the system 700 can, in various embodiments, comprise the same components as the system 400, and can further comprise a heatmap component 702.

In various embodiments, the heatmap component 702 can employ a second machine learning and/or deep learning algorithm that can generate a heatmap showing the key points or anatomical masks of the detected person based on the bounding box and that can accordingly localize the face or facial region of the detected person based on the key points or anatomical masks in the heatmap. In various aspects, the second machine learning and/or deep learning algorithm can output coordinates and/or approximate coordinates of the key points or anatomical masks of the detected person in the frame (e.g., coordinates corresponding to the locations of the shoulders of the detected person, coordinates corresponding to the locations of the hips of the detected person, coordinates corresponding to the locations of the eyes, ears, and nose of the detected person, and so on). In various aspects, the second machine learning and/or deep learning algorithm can provide a plurality of key point predictions throughout the bounding box, and the highest predictions can be taken as the inferred locations of the relevant key points or anatomical masks (e.g., multiple predicted/possible locations for a right shoulder, where the highest/prediction is taken as the inferred location of the right shoulder, and so on). The outputted coordinates that correspond to the face or facial region of the detected person can then be used (e.g., by the anonymization component 114) to determine which pixels in the frame to anonymize (e.g., blur those pixels that are within a predetermined distance of the coordinates of the face or facial region of the detected person, and so on).

In various embodiments, the second machine learning and/or deep learning algorithm can estimate and/or infer a location of a facial region of the detected person even if the face or facial region is partially occluded (e.g., by medical headgear, by clothing, by other objects, and so on), based on the locations/orientations of other, visible key points or anatomical masks of the detected person. For example, if a patient is depicted in a frame as wearing an MRI headset such that their eyes, ears, nose, and/or chin are not fully visible in the frame, the second machine learning and/or deep learning algorithm can, in various embodiments, estimate and/or infer the location of their head/face or facial region based on the known locations and orientations of the visible key points or anatomical masks. For instance, since the shoulders, hips, knees, and/or elbows of the detected patient are visible and are relatively positioned in a way that is consistent with the head/face or facial region of the person being within and/or behind the MRI headset, the second machine learning and/or deep learning algorithm can infer that the face or facial region/head of the person is visually blocked by the depicted MRI headset and can thus place the facial key points or anatomical masks of the heatmap over the MRI headset anyway. That is, in various embodiments, the second machine learning and/or deep learning algorithm can accurately predict key point locations/coordinates even if the detected person's body and/or face or facial region are partially occluded.

In various embodiments, the second machine learning and/or deep learning algorithm can include any suitable mathematical, statistical, and/or computational technique that can be trained (e.g., via supervised learning) to recognize and/or classify patterns depicted in images (e.g., to recognize body orientation in a bounding box and to classify identified key points or anatomical masks as shoulders, knees, ankles, eyes, ears, and so on). In various embodiments, a second machine learning and/or deep learning algorithm can comprise one or more linear classifiers (e.g., generative classifiers such as Naïve Bayes, linear discriminant analysis, and so on; discriminative classifiers such as logistic regression, perceptron, support vector machines, and so on; linear affine transformations optimized to achieve global minima; and so on). In various embodiments, a second machine learning and/or deep learning algorithm can comprise one or more non-linear classifiers (e.g., artificial neural networks, non-linear and/or high dimensional support vector machines, and so on). As mentioned above, the second machine learning and/or deep learning algorithm can, in various embodiments, comprise a Simple Pose ResNet algorithm, which is a type of neural network designed to visually predict locations/coordinates of primary joints and facial features of a depicted human. In various embodiments, a Simple Pose ResNet 50 can be utilized (e.g., a 50-layer residual neural network). In various embodiments, a Simple pose ResNet 101 can be utilized (e.g., a 101-layer residual neural network). In various aspects, a Simple Pose ResNet algorithm can include GluonCV for key point and pose estimation, and can be trained by transfer learning.

In various embodiments, a Simple Pose ResNet algorithm can have particular formatting requirements for input images (e.g., expecting an image that is 256 pixels×192 pixels where the human is centered in the image). To comply with such formatting requirements, the bounding box generated by the YOLOv3 object detection algorithm can be used as the input image. In various aspects, the bounding box can already be substantially centered around the detected person (e.g., the object detection algorithm can be trained to accomplish this), and the bounding box can be cropped, resized, and/or normalized as needed/desired to facilitate analysis by the Simple Pose ResNet algorithm.

Figure 9:
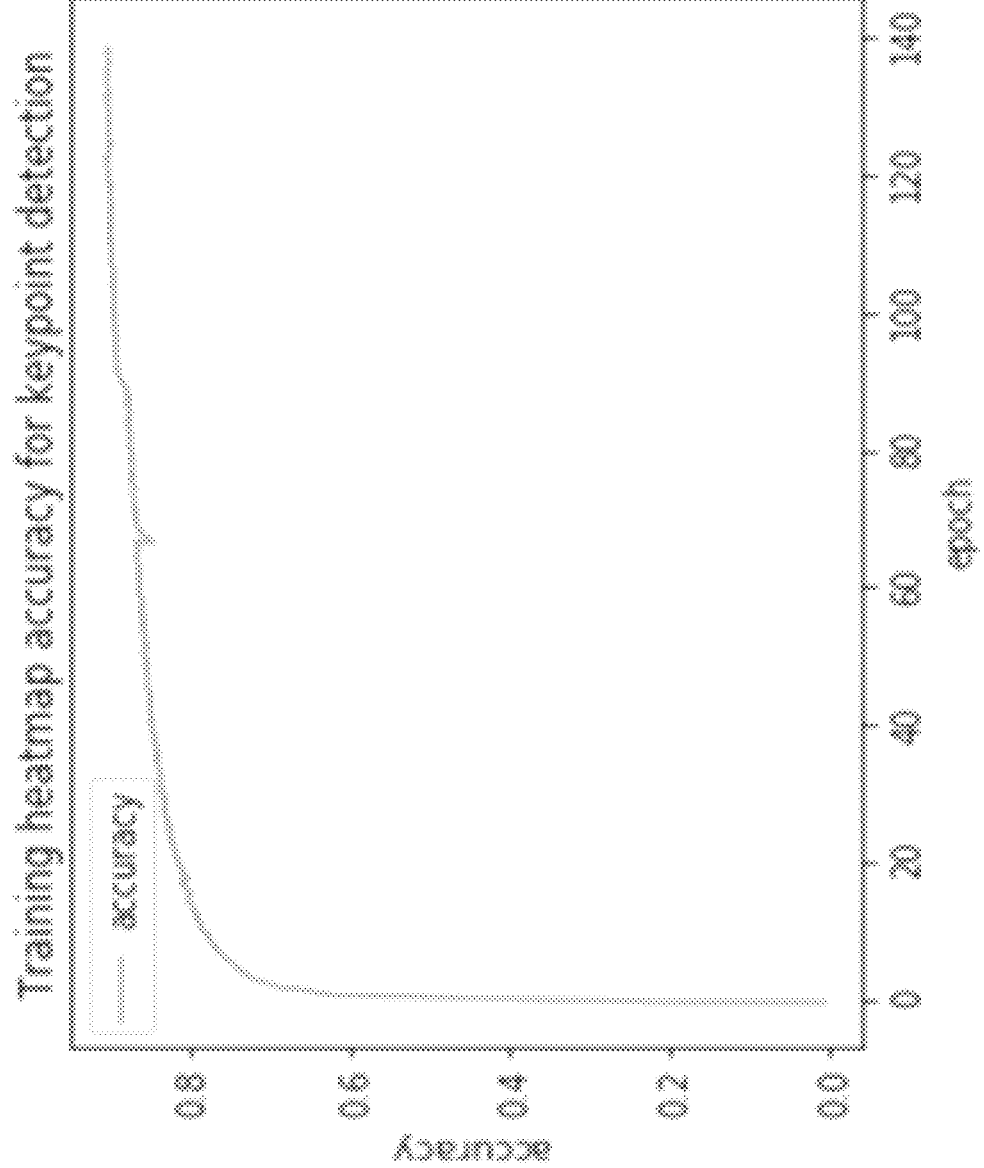

FIGS. 8-9 illustrate example, non-limiting graphs 800 and 900 depicting training results of a heatmap component including a Simple Pose ResNet algorithm in a system that can facilitate automated facial anonymization/de-identification in regular and/or occluded video streams obtained during diagnostic medical procedures in accordance with one or more embodiments described herein.

As shown, the graphs 800 depict Training Loss per epoch for both a Simple Pose ResNet 50 and a Simple Pose Resent 101.

As shown, the graph 900 depicts heatmap accuracy per epoch for a Simple Pose ResNet 101. In various instances, after 140 epochs, the trained Simple Pose ResNet 101 exhibited a heatmap accuracy of 0.9 and a training loss of 0.000270.

Figure 10:
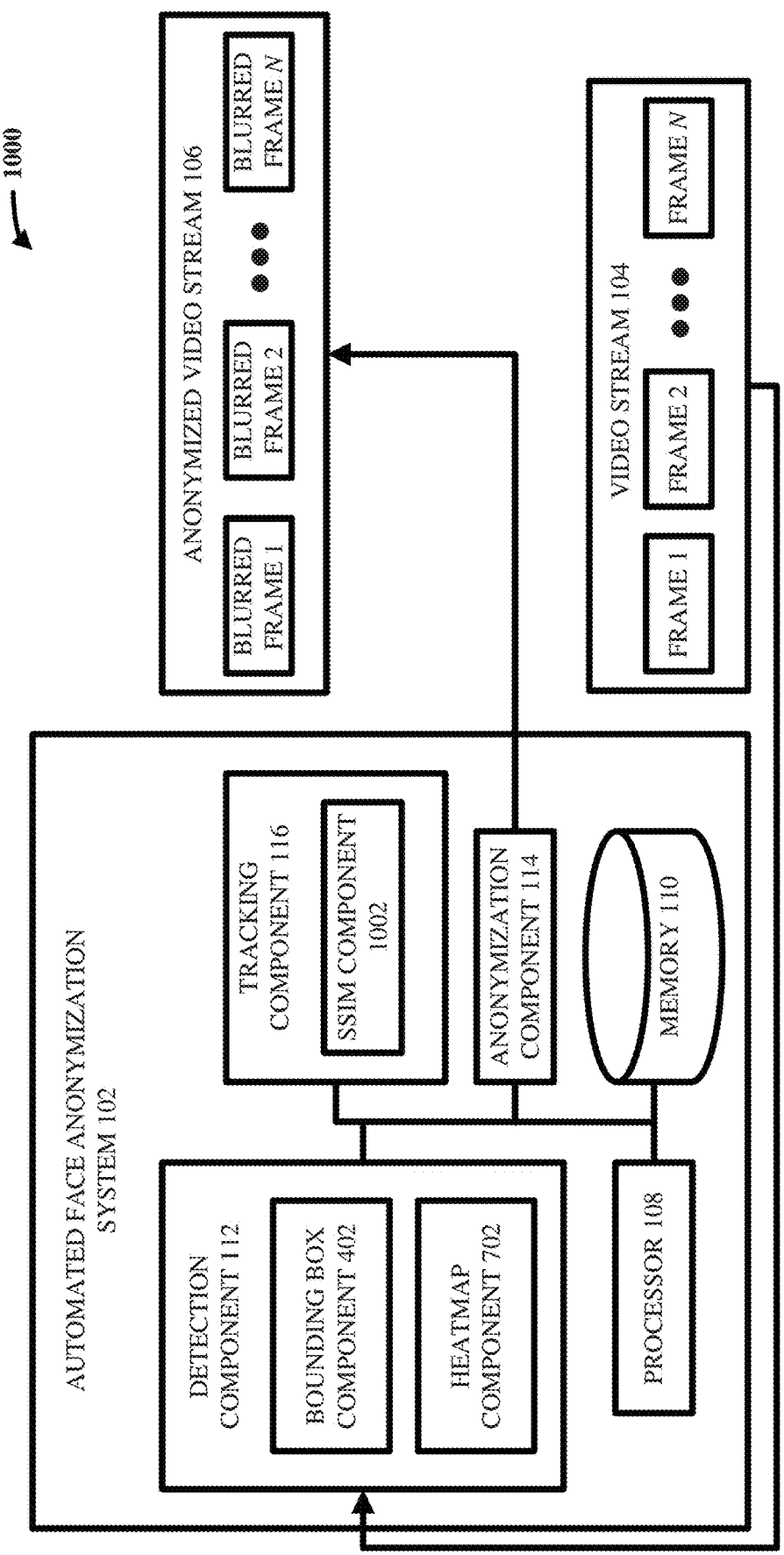
FIG. 10 illustrates a block diagram of an example, non-limiting system including an SSIM component that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 10 illustrates a block diagram of an example, non-limiting system 1000 including an SSIM component that can facilitate automated facial anonymization/de-identification in regular and/or occluded video streams obtained during diagnostic medical procedures in accordance with one or more embodiments described herein. As shown, the system 1000 can, in various embodiments, comprise the same components as the system 700, and can further comprise an SSIM component 1002.

As mentioned above, the SSIM component 1002 can compute a structural similarity index (SSIM) between two frames/images, if tracking has been initialized. If the computed SSIM between a current frame and an immediately-previous, anonymized frame is greater than and/or equal to a predetermined threshold, the tracking component 116 can localize one or more face or facial regions in the current frame without running the time-consuming and/or computationally expensive object detection and pose estimation algorithms (e.g., YOLOv3 and Simple Pose ResNet). This can result in an automated facial anonymization system that is robust and accurate as well as quick and efficient. In various aspects, such a system can perform fault-tolerant facial de-identification at sufficiently high frame rates (e.g., about 30 frames per second) so as to enable processing of real-time and/or near real-time video streams.

An SSIM is a mathematical measure of similarity between two images. In various instances, an SSIM can be considered as a full reference metric in which one of the frames is considered as of perfect quality and another of the frames is being analyzed to determine how much it differs from the reference frame. In various aspects, SSIM can be defined as a weighted product of luminance (l) between two images A and B with weight α, contrast (c) between two images A and B with weight β, and structure (s) between two images A and B with weight γ. That is:

$$SSIM = l(A,B)^{\alpha} * c(A,B)^{\beta} * s(A,B)^{\gamma}$$

In various embodiments, luminance, contrast, and structure can be defined as follows:

$$l(A, B) = \frac{2\mu_A\mu_B + c_1}{\mu_A^2 + \mu_B^2 + c_1}$$

$$c(A, B) = \frac{2\sigma_A\sigma_B + c_2}{\sigma_A^2 + \sigma_B^2 + c_2}$$

$$s(A, B) = \frac{\sigma_{AB} + c_3}{\sigma_A\sigma_B + c_3}$$

where $\mu_A$ is the average of frame A (and/or the average pixel value of a sub-window of frame A), $\mu_B$ is the average of frame B (and/or the average pixel value of a corresponding sub-window of frame B), $\sigma_A^2$ is the variance of frame A (and/or the variance of the sub-window of frame A), $\sigma_B^2$ is the variance of frame B (and/or the variance of the sub-window of frame B), $\sigma_{AB}$ is the covariance of A and B (and/or the covariance of the sub-windows of A and B), and $c_1$, $c_2$, and $c_3$ are constants dependent on the dynamic range of the pixel-values. The above formulas are illustrative and exemplary only. In various embodiments, other mathematical definitions and/or formulations of SSIM can be incorporated.

In various embodiments, any other suitable mathematical measure of similarity between two images can be implemented (e.g., peak signal-to-noise ratio, mean squared error, sum of squared error, and so on).

Figure 11:
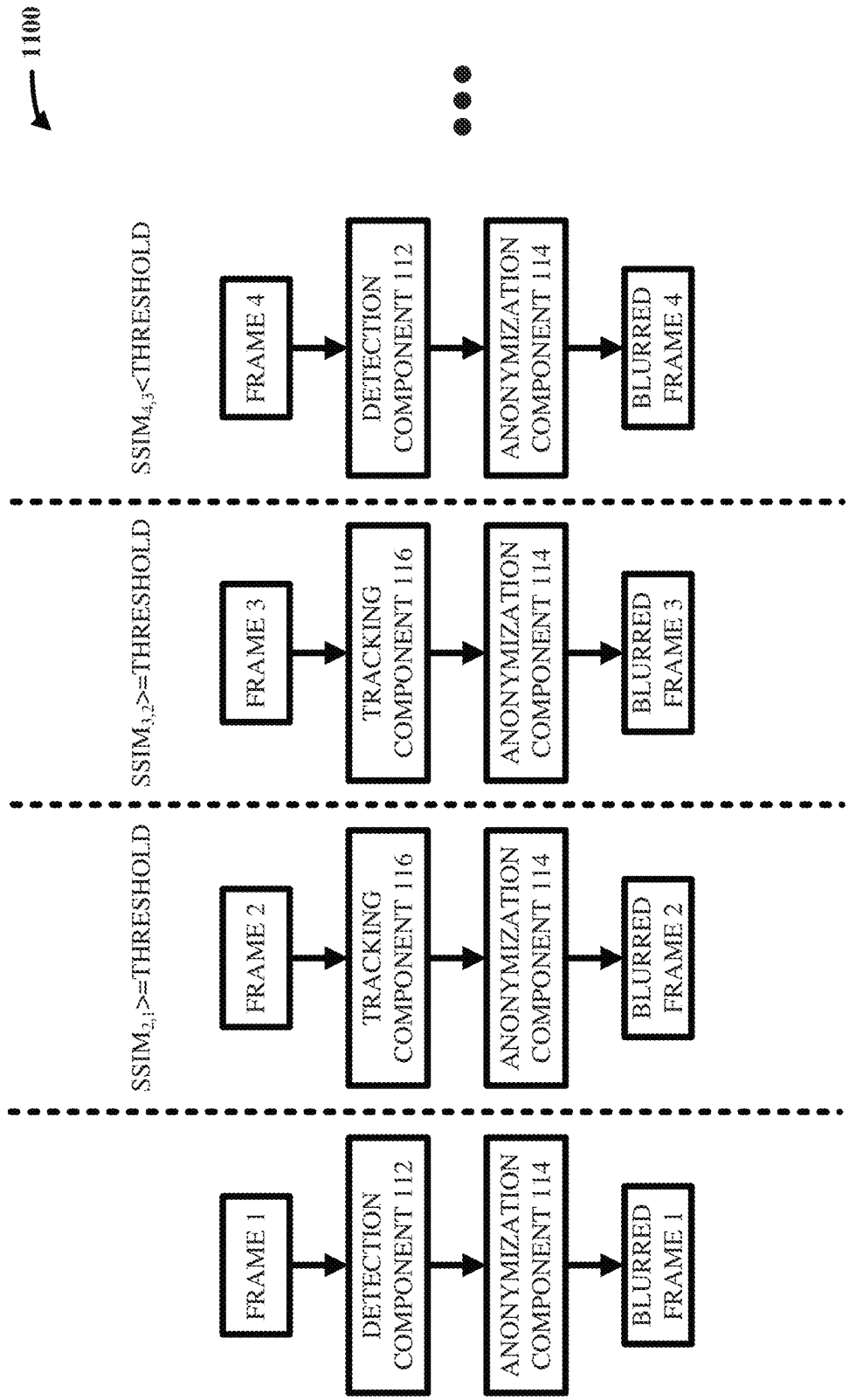
FIG. 11 illustrates an exemplary, non-limiting diagram of an SSIM component determining whether a tracking algorithm should be run on a frame in accordance with one or more embodiments described herein.

FIG. 11 illustrates an exemplary, non-limiting diagram 1100 of an SSIM component determining whether a tracking algorithm should be run on a frame in accordance with one or more embodiments described herein.

As shown in FIG. 11, frame 1 from the video stream 104 can be extracted by the automated face anonymization system 102. Since tracking can be uninitialized by default, frame 1 can be processed by the detection component 112 (e.g., bounding box and heatmap generated to localize face or facial region). As mentioned above, the detection component 112 can initialize tracking after successfully localizing a face or facial region in a frame. After the one or more face or facial regions depicted in frame 1 are localized by the detection component 112, the anonymization component 114 can pixilate/blur the face or facial regions. This can result in blurred frame 1.

Next, frame 2 from the video stream 104 can be extracted by the automated face anonymization system 102. Since the detection component 112 initialized tracking, the tracking component 116 can compute, via the SSIM component 1002, an SSIM between frame 2 and frame 1 (e.g., the immediately-preceding and anonymized frame). As shown in FIG. 11, the $SSIM_{2,1}$ can be greater than and/or equal to the threshold. Since the $SSIM_{2,1}$ is greater than and/or equal to the threshold, frame 2 can be considered as sufficiently structurally similar to frame 1, and so frame 2 can be processed by the tracking component 116 (e.g., tracking in frame 2 of the one or more face or facial regions that were localized and anonymized in frame 1). The anonymization component 114 can then blur the one or more face or facial regions, and the result can be stored/streamed as blurred frame 2.

Next, frame 3 from the video stream 104 can be extracted by the automated face anonymization system 102. Note that tracking was not reset/uninitialized during the processing of frame 2. Thus, tracking can still be initialized, meaning that the tracking component 116 can compute, via the SSIM component 1002, an SSIM between frame 3 and frame 2 (e.g., the immediately-preceding and anonymized frame). As shown in FIG. 11, the $SSIM_{3,2}$ can be greater than and/or equal to the threshold. Since the $SSIM_{3,2}$ is greater than and/or equal to the threshold, frame 3 can be considered as sufficiently structurally similar to frame 2, and so frame 3 can be processed by the tracking component 116 (e.g., tracking in frame 3 of the one or more face or facial regions that were localized and anonymized in frame 2). The anonymization component 114 can then blur the one or more face or facial regions, and the result can be stored/streamed as blurred frame 3.

Next, frame 4 from the video stream 104 can be extracted by the automated face anonymization system 102. Note that tracking was not reset/uninitialized during the processing of frame 3. Thus, tracking can still be initialized, meaning that the tracking component 116 can compute, via the SSIM component 1002, an SSIM between frame 4 and frame 3 (e.g., the immediately-preceding and anonymized frame). As shown in FIG. 11, the $SSIM_{4,3}$ can be less than the threshold (e.g., due to sudden change in illumination, sudden camera movement, sudden appearance of additional people, and so on). Since the $SSIM_{4,3}$ is less than the threshold, frame 4 can be considered as insufficiently structurally similar to frame 3. So the tracking component 116 can reset/uninitialize tracking, and frame 4 can be processed by the detection component 112 (e.g., bounding box and heat-map generated to localize face or facial regions) rather than by the tracking component 116. As above, the anonymization component 114 can blur the one or more localized face or facial regions in frame 4, and the result can be stored/streamed as blurred frame 4. Additional/subsequent frames can be extracted and processed in this fashion.

Overall, FIG. 11 demonstrates that various embodiments of the subject claimed innovation can determine whether to analyze an extracted frame using the detection component 112 or using the tracking component 116 based on the computed SSIM. If the current frame is sufficiently similar to the immediately-previous and anonymized frame (e.g., if the SSIM is greater than and/or equal to the threshold), the tracking component 116 can localize the one or more face or facial regions in the frame via tracking, thereby saving time and expending fewer computing resources than if the detection component 112 had localized the face or facial regions in the frame via object detection and pose estimation. Since the SSIM is sufficiently high, the accuracy of the tracking component 116 can be acceptable. However, if the current frame is instead insufficiently similar to the immediately-previous and anonymized frame (e.g., if the SSIM is less than the threshold), the detection component 112 can localize the one or more face or facial regions in the frame. Although this requires additional time and resources as compared to the tracking component 116, it can, in various embodiments, be worth it since the tracking algorithm of the tracking component 116 can exhibit lower and/or unacceptable accuracy when analyzing frames having too low of an SSIM.

In this way, embodiments of the subject claimed innovation can provide for a robust yet efficient anonymization system/technique that expends additional time and resources on object detection and pose estimation only when required (e.g., only when the SSIM does not satisfy the threshold), rather than employing object detection and pose estimation for every single frame in a video stream. For all other frames (e.g., where the SSIM is sufficiently high), acceptable anonymization accuracy can be obtained more quickly and more efficiently by localizing face or facial regions using a trained tracking algorithm of the tracking component 116.

Figure 12:
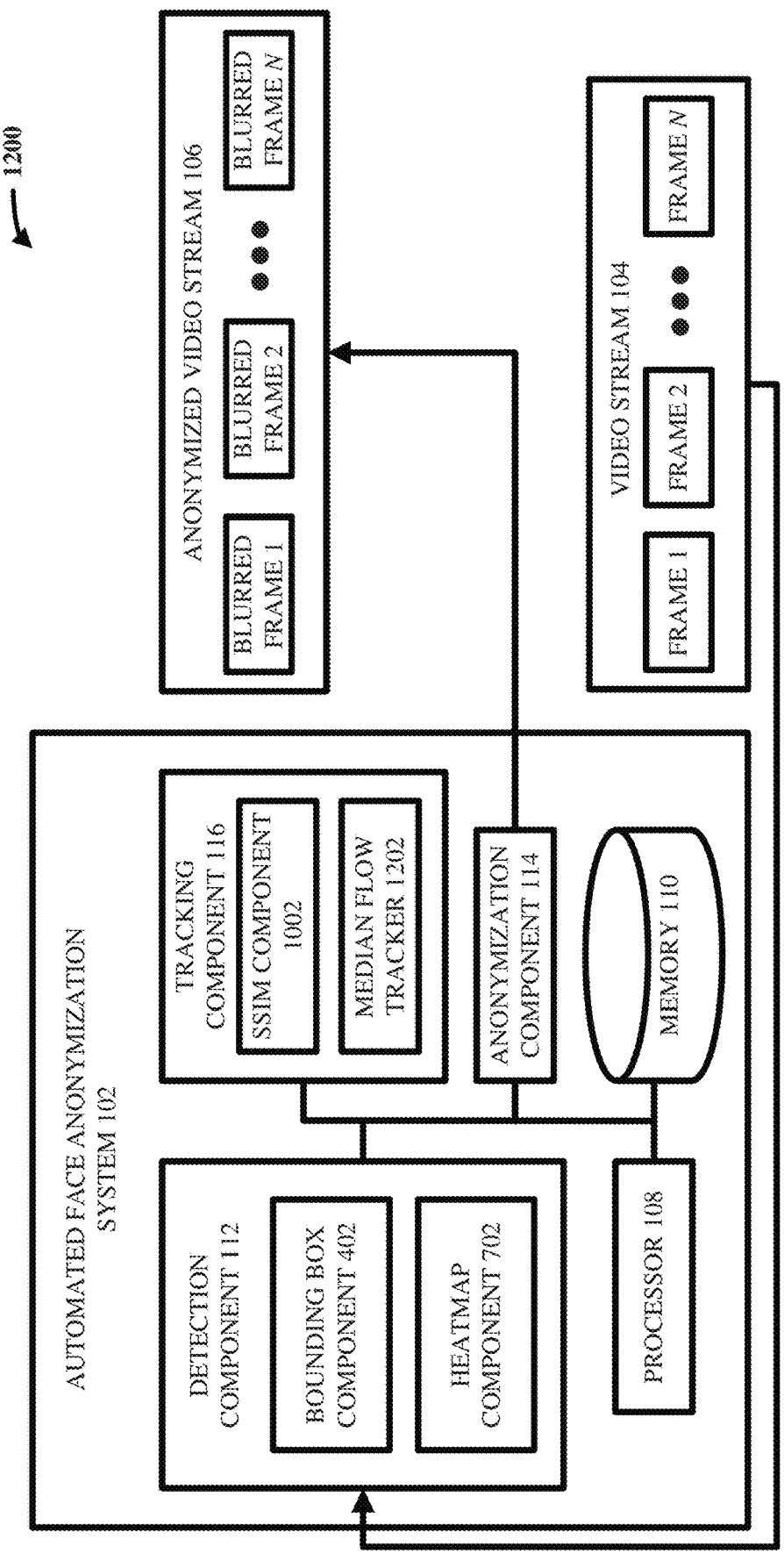
FIG. 12 illustrates a block diagram of an example, non-limiting system including a median flow tracker that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 12 illustrates a block diagram of an example, non-limiting system 1200 including a median flow tracker that can facilitate automated facial anonymization/de-identification in regular and/or occluded video streams obtained during diagnostic medical procedures in accordance with one or more embodiments described herein. As shown, the system 1200 can, in various embodiments, comprise the same components as the system 1000, and can further comprise a median flow tracker 1202.

In various embodiments, the median flow tracker 1202 can receive as input the locations/coordinates determined to correspond to one or more face or facial regions localized in the immediately-previous, anonymized frame, and can compare the current frame with the immediately-previous, anonymized frame to determine trajectories of the localized face or facial regions. In various embodiments, this allows the one or more face or facial regions to be tracked in a subsequent frame without having to re-run the costly and/or time-consuming object detection and pose estimation algorithms of the detection component 112. As mentioned above, the accuracy of the median flow tracker 1202 can be acceptable if the SSIM between the current frame and the immediately-preceding, anonymized frame satisfies the predetermined threshold. As mentioned above, the predetermined threshold can be any suitable and/or desired level, and can depend on operational context. In various instances, the inventors of the subject claimed innovation have found that a threshold 0.8 (e.g., 80%) can offer an acceptable balance of speed and tracking accuracy. In various aspects, however, any other suitable value can be chosen as desired.

In various aspects, the median flow tracker 1202 can receive a pair of consecutive images (e.g., a current frame and an immediately-previous, anonymized frame) as well as a bounding box in the previous frame that circumscribes the object to be tracked (e.g., a bounding box with substantially minimal interior area that substantially circumscribes a face or facial region to be tracked). As mentioned above, the detection component 112, via the bounding box component 402, can generate a bounding box substantially around a detected person in a frame. In various instances, this body bounding box can be received by the median flow tracker to track the entire body of the detected person in a subsequent, sufficiently similar frame. In various embodiments, the detection component 112 can generate, after localizing a face or facial region of a detected person, a second bounding box with substantially minimal interior area and which substantially circumscribes only the face or facial region of the detected person. In various instances, this face or facial region bounding box (e.g., not depicted in the FIGs.) can be received by the median flow tracker 1202 to track the face or facial region of the detected person in a subsequent, sufficiently similar frame. Based on the inputted frames and the inputted bounding box (e.g., the face or facial region bounding box), the median flow tracker 1202 can output an updated bounding box (e.g., updated face or facial region bounding box) in the subsequent frame that estimates a new location of the tracked object (e.g., the face or facial region). Specifically, in various embodiments, a set of points can be initialized on a rectangular grid within the initial frame's bounding box (e.g., the face or facial region bounding box). These points can then be tracked by a Lucas-Kanade tracker (and/or any other suitable tracking technique), which can generate a sparse motion flow between the two frames. The quality of the point predictions can be estimated by assigning each point an error. In various aspects, a forward-backward error value can be used (e.g., tracking the object in both forward and backward directions/trajectories in time to measure discrepancies between the trajectories). In various aspects, minimizing this forward-backward error can result in reliable tracking of desired objects (e.g., face or facial regions). In various embodiments, any other suitable error measurement can be used (e.g., normalized cross correlation, sum-of-square differences, and so on). In various aspects, a portion (e.g., 50%) of the worst predictions can be filtered out, and the remaining predictions can be used to estimate the displacement of the whole bounding box (e.g., the face or facial region bounding box). In this way, the median flow tracker 1202 can determine a new/updated location of the face or facial region bounding box, meaning that the face or facial region of the detected person can be localized/tracked in the subsequent frame without requiring the full object detection and pose estimation algorithms of the detection component 112.

In various aspects, when processing real-time and/or near real-time video streams, the frame-wise facial localization of the detection component 112 (e.g., the object detection and pose estimation algorithms) can result in a frame rate of approximately 12 to 15 frames per second. Processing each and every frame in a real-time video stream at such a rate can, in various instances, result in unacceptable video quality (e.g., unsmooth/jerky motion, and so on). In various aspects, facial localization via appearance-based tracking by the tracking component 116 (e.g., SSIM component 1002 and median flow tracker 1202) can result in a frame rate of approximately 30 frames per second, as confirmed by experiments conducted by the inventors of the subject claimed innovation. In various aspects, this can amount to a doubling of performance as compared to existing facial anonymization systems/techniques, thereby yielding superior real-time video stream quality.

In various embodiments, any other suitable appearance-based tracking algorithm can be implemented (e.g., GOTURN tracker, and so on). In various aspects, GOTURN trackers can result in higher frame rates, at the expense of less reliable/robust tracking accuracy (e.g., GOTURN trackers can be more vulnerable to illumination changes and/or background clutter than can Median Flow trackers).

In various embodiments, any suitable number of median flow trackers and/or GOTURN trackers can be implemented as desired (e.g., one tracker per object to be tracked, one tracker to track all objects to be tracked, and so on).

Figure 13:
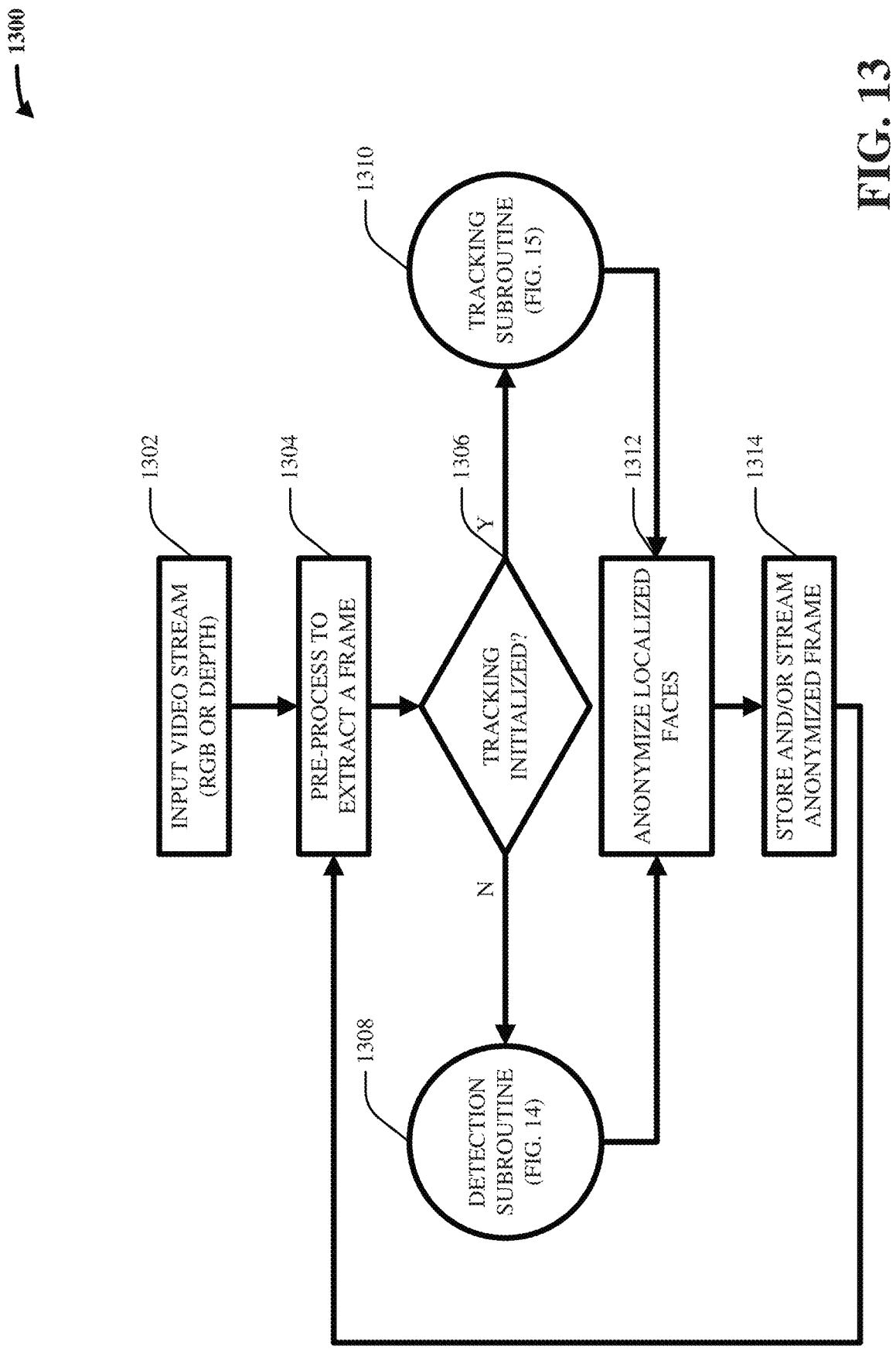
FIG. 13 illustrates a high-level flow diagram of an example, non-limiting computer-implemented method that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 13 illustrates a high-level flow diagram of an example, non-limiting computer-implemented method 1300 that can facilitate automated facial anonymization/de-identification in regular and/or occluded video streams obtained during diagnostic medical procedures in accordance with one or more embodiments described herein.

In various embodiments, act 1302 can include inputting, by a device operatively coupled to a processor, a video stream (e.g., video stream 104). In various cases, the video stream can be color frames (e.g., RGB) and/or can be depth frames.

In various instances, act 1304 can include pre-processing, by the device, the video stream to extract a frame (e.g., frame 1). In various cases, a camera health check can be included in this pre-processing (e.g., checking whether RGB, depth, and/or infrared streaming is achieved; checking for camera firmware updates; troubleshooting camera connectivity, field of view/vision, and electrical connections as needed; calibrating the color, infrared, and/or 3D depth cameras and obtaining intrinsic and/or extrinsic calibration parameters; performing camera to world coordinate conversion via rotation and homogenous transformation matrices; and so on). In various embodiments, this pre-processing can include segmentation of facial and body regions in RGB images using depth frames as references (e.g., segmentation of face or facial region and body in RFB can be performed based on cues from depth frames).

In various aspects, act 1306 can include determining, by the device, whether tracking is initialized. If so, the computer-implemented method 1300 can proceed to the tracking subroutine 1310 (e.g., described in FIG. 15) to localize one or more face or facial regions in the extracted frame. If not, the computer-implemented method 1300 can proceed to the detection subroutine 1308 (e.g., described in FIG. 14) to localize one or more face or facial regions in the extracted frame.

In various embodiments, act 1312 can include anonymizing, by the device, the one or more localized face or facial regions in the extracted frame.

In various instances, act 1314 can include storing and/or streaming, by the device, the anonymized frame (e.g., as a blurred frame in the anonymized video stream 106).

As mentioned above, the computer-implemented method 1300 can achieve robust and accurate facial anonymization by implementing the detection subroutine 1308 when needed (e.g., when SSIM does not satisfy the predetermined threshold) and can achieve fast and efficient anonymization by implementing the tracking subroutine 1310 otherwise (e.g., when SSIM does satisfy the predetermined threshold).

Figure 14:
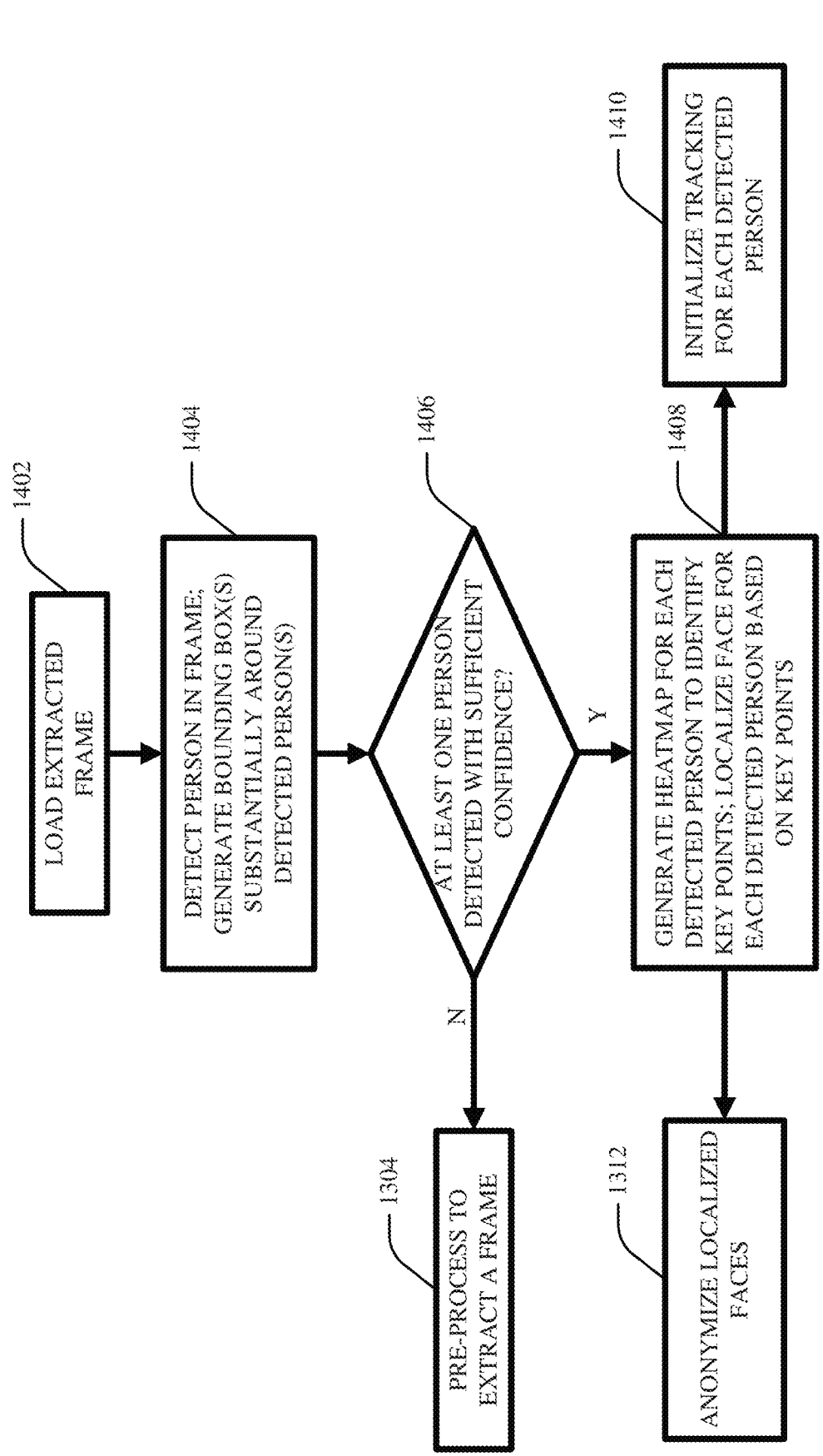
FIG. 14 illustrates a high-level flow diagram of an example, non-limiting computer-implemented method of a detection subroutine that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 14 illustrates a high-level flow diagram of an example, non-limiting computer-implemented method 1400 of a detection subroutine that can facilitate automated facial anonymization/de-identification in regular and/or occluded video streams obtained during diagnostic medical procedures in accordance with one or more embodiments described herein. That is, the computer-implemented method 1400 can be considered the detection subroutine 1308.

In one or more embodiments, act 1402 can include loading, by the device, the extracted frame.

In various instances, act 1404 can include detecting, by the device, one or more persons in the frame and generating one or more bounding boxes substantially around the detected persons (e.g., via the bounding box component 402). In various cases, this act can include outputting a confidence level associated with each bounding box, as described above.

In various aspects, act 1406 can include determining, by the device, whether at least one person was detected with sufficient confidence. If not, the computer-implemented method 1400 can proceed to act 1304 (e.g., no person was detected in the frame, which means that anonymization is not required and so another frame can be extracted). If so, the computer-implemented method 1400 can proceed to act 1408.

In various embodiments, act 1408 can include generating, by the device, a heatmap for each detected person based on the bounding boxes (e.g., via the heatmap component 702) in order to identify key points or anatomical masks of the detected persons. Act 1408 can also include localizing the face or facial regions of the detected persons based on the key points or anatomical masks (e.g., determining the locations/coordinates in the frame of the face or facial regions of the detected persons). The computer-implemented method 1400 can, in various cases, then proceed to both act 1312 (e.g., anonymization of the localized face or facial regions) and to act 1410.

In various instances, act 1410 can include initializing, by the device, tracking for each detected person.

Figure 15:
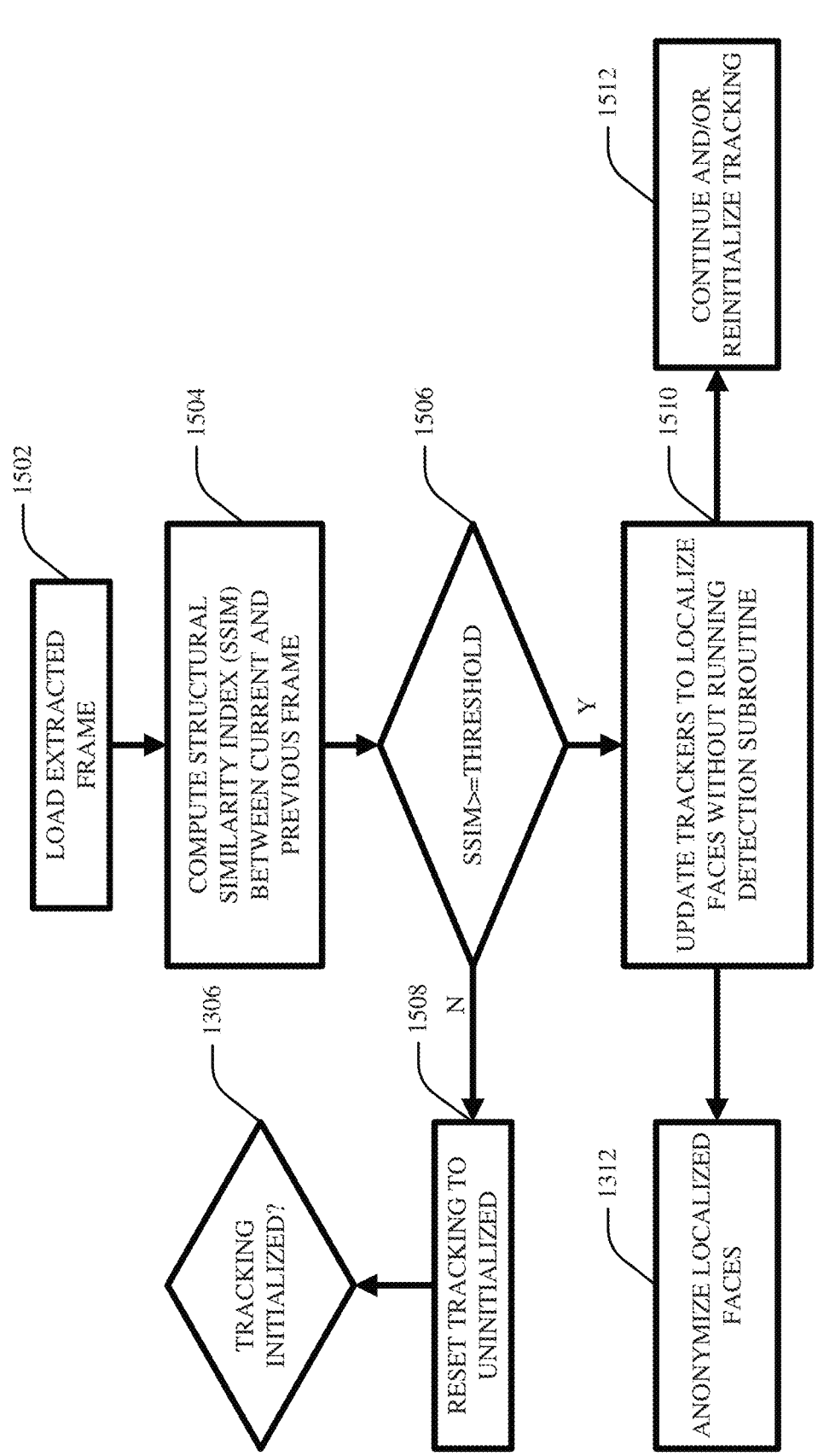
FIG. 15 illustrates a high-level flow diagram of an example, non-limiting computer-implemented method of a tracking subroutine that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 15 illustrates a high-level flow diagram of an example, non-limiting computer-implemented method 1500 of a tracking subroutine that can facilitate automated facial anonymization/de-identification in regular and/or occluded video streams obtained during diagnostic medical procedures in accordance with one or more embodiments described herein. That is, the computer-implemented method 1500 can be considered the tracking subroutine 1310.

In various embodiments, act 1502 can include loading, by the device, the extracted frame.

In various instances, act 1504 can include computing, by the device, a structural similarity index (SSIM) between the current frame and the immediately-previous, anonymized frame (e.g., via the SSIM component 1002).

In various aspects, act 1506 can include determining, by the device, whether the SSIM is greater than and/or equal to a predetermined threshold. If not, the computer-implemented method 1500 can proceed to act 1508. If so, the computer-implemented method 1500 can proceed to act 1510.

In various embodiments, act 1508 can include resetting, by the device, tracking to uninitialized. The computer-implemented method 1500 can then proceed to act 1306 of the computer-implemented method 1300.

In various instances, act 1510 can include updating, by the device, one or more trackers (e.g., median flow tracker 1202) to localize one or more face or facial regions (e.g., the face or facial regions that were localized and anonymized in the immediately-previous, anonymized frame) without running the detection subroutine (e.g., without running the object detection and pose estimation algorithms of the detection component 112). The computer-implemented method 1500 can then proceed to both act 1312 (e.g., to anonymize the localized/tracked face or facial regions) and to act 1512.

In various aspects, act 1512 can include continuing and reinitializing, by the device, tracking.

In various embodiments, the tracking subroutine can be run until the SSIM falls below the threshold, at which point the detection subroutine can be performed. As explained thoroughly above, the detection subroutine (e.g., FIG. 14) can allow embodiments of the subject claimed innovation to perform robust and accurate facial localization in unfamiliar frames (e.g., when SSIM is below the threshold), and the tracking subroutine (e.g., FIG. 15) can allow embodiments of the subject claimed innovation to perform sufficiently accurate (e.g., no significant drop in accuracy) and fast facial localization in familiar frames (e.g., when SSIM is greater than and/or equal to the threshold). Such embodiments exhibit superior and fault tolerant anonymization at frames rates that are high enough to facilitate processing of real-time videos streams (e.g., about 30 frames per second).

FIGS. 16-22 illustrate example, non-limiting frames outputted by a system that can facilitate automated facial anonymization/de-identification in regular and/or occluded video streams obtained during diagnostic medical procedures in accordance with one or more embodiments described herein. That is, FIGS. 16-22 illustrate final and/or intermediate anonymized frames outputted by embodiments of the subject claimed innovation and which emphasize the robust and fault tolerant nature of embodiments of the subject claimed innovation.

Figure 16:
FIGS. 16-22 illustrate example, non-limiting frames outputted by a system that facilitates automated facial anonymization/de-identification in regular and/or occluded video streams (e.g., RGB, RGBA8, YUYV and all supported color formats) obtained during diagnostic medical procedures in accordance with one or more embodiments described herein.
Figure 17:

FIGS. 16-17 illustrate final anonymized frames of patients wearing MRI head coils. As shown in both images, embodiments of the subject claimed innovation were able to accurately localize and anonymize the face or facial regions of the patients even though their face or facial regions were partially occluded by the MRI head coils.

Figure 18:
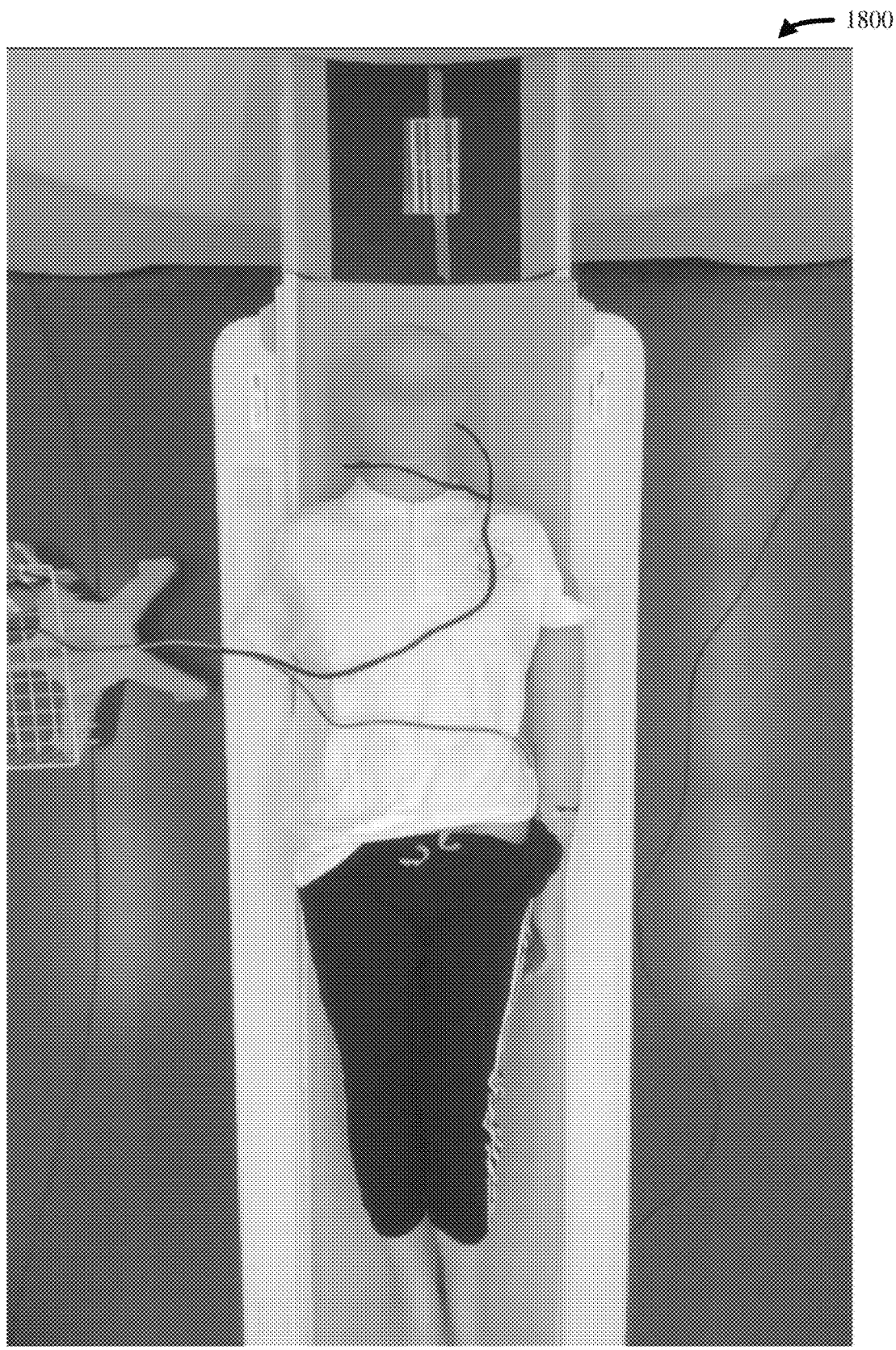

FIG. 18 illustrates a final anonymized frame of a medical dummy lying on a medical apparatus. As shown, embodiments of the subject claimed innovation were able to accurately localize and anonymize the face or facial region of the medical dummy, notwithstanding the reflective surface or facial regions/skin of the medical dummy (e.g., emphasizing robustness of the subject claimed innovation).

Figure 19:

FIG. 19 illustrates a final anonymized frame of a patient lying on a medical apparatus with his body partially occluded/covered by a medical blanket. As shown, embodiments of the subject claimed innovation were able to accurately localize and anonymize the face or facial region of the patient, even though the patient's body is substantially occluded by the medical blanket.

Figure 20:
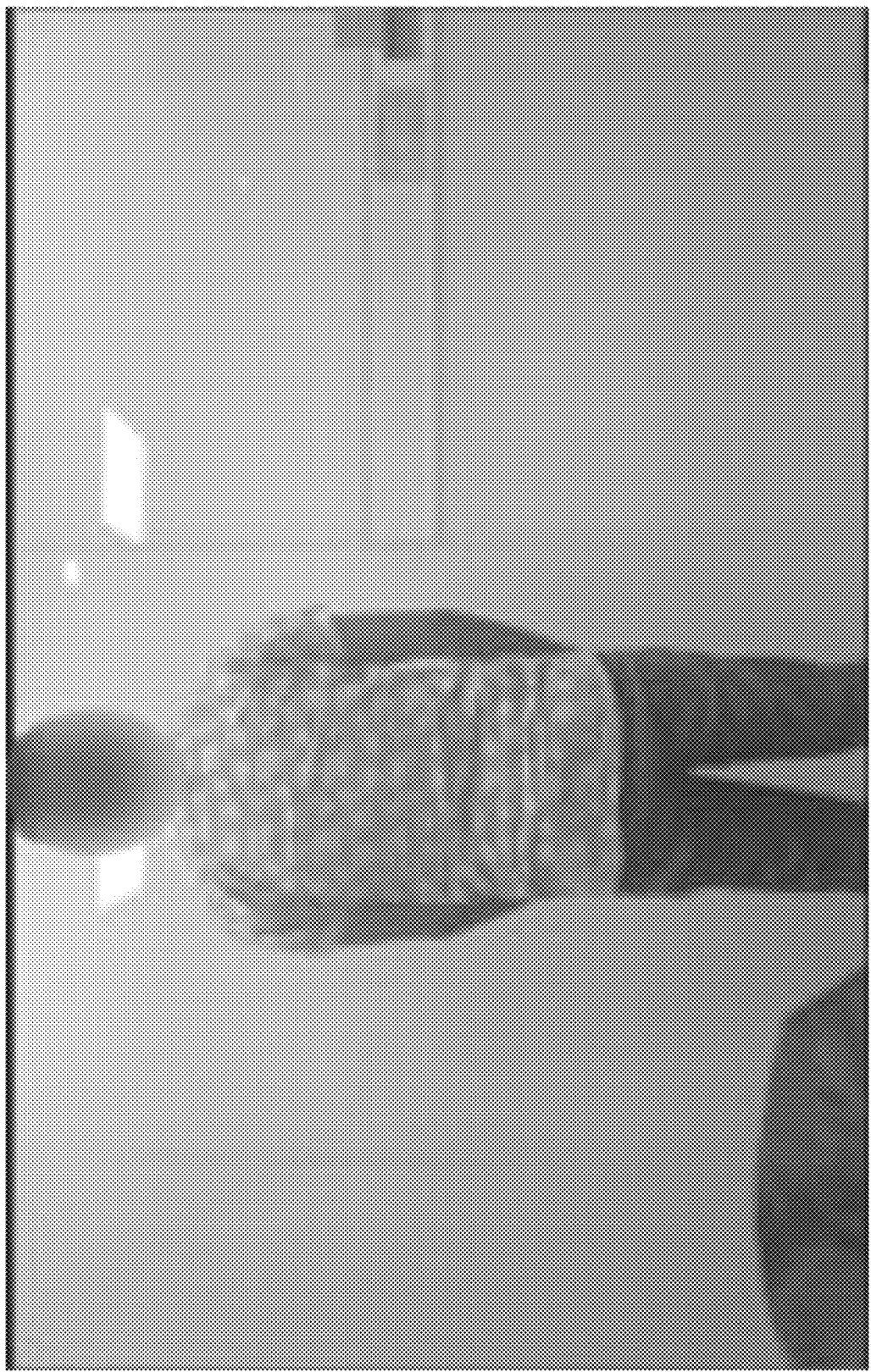

FIG. 20 illustrates a final anonymized frame of a patient facing away from the camera (e.g., posterior-anterior view). As shown, embodiments of the subject claimed innovation were able to accurately localize and anonymize the facial region of the patient, even though the patient's face or facial region was turned around and/or facing completely away from the camera.

Figure 21:

FIG. 21 illustrates a final anonymized frame of a patient's lateral right side facing the camera with her right arm partially occluding her face or facial region. As shown, embodiments of the subject claimed innovation were able to accurately localize and anonymize the face or facial region of the patient, even though only the patient's right profile side was visible and even though her face or facial region was partially occluded by her right arm. Moreover, as shown, embodiments of the subject claimed innovation were able to prevent over-anonymization. Indeed, only that portion of the patient's face or facial region that is visible in the frame is anonymized (e.g., the top, right portion of her face or facial region). Even though part of the patient's face or facial region is behind her right arm, pixels corresponding to the right arm and/or right shoulder were not anonymized.

Figure 22:
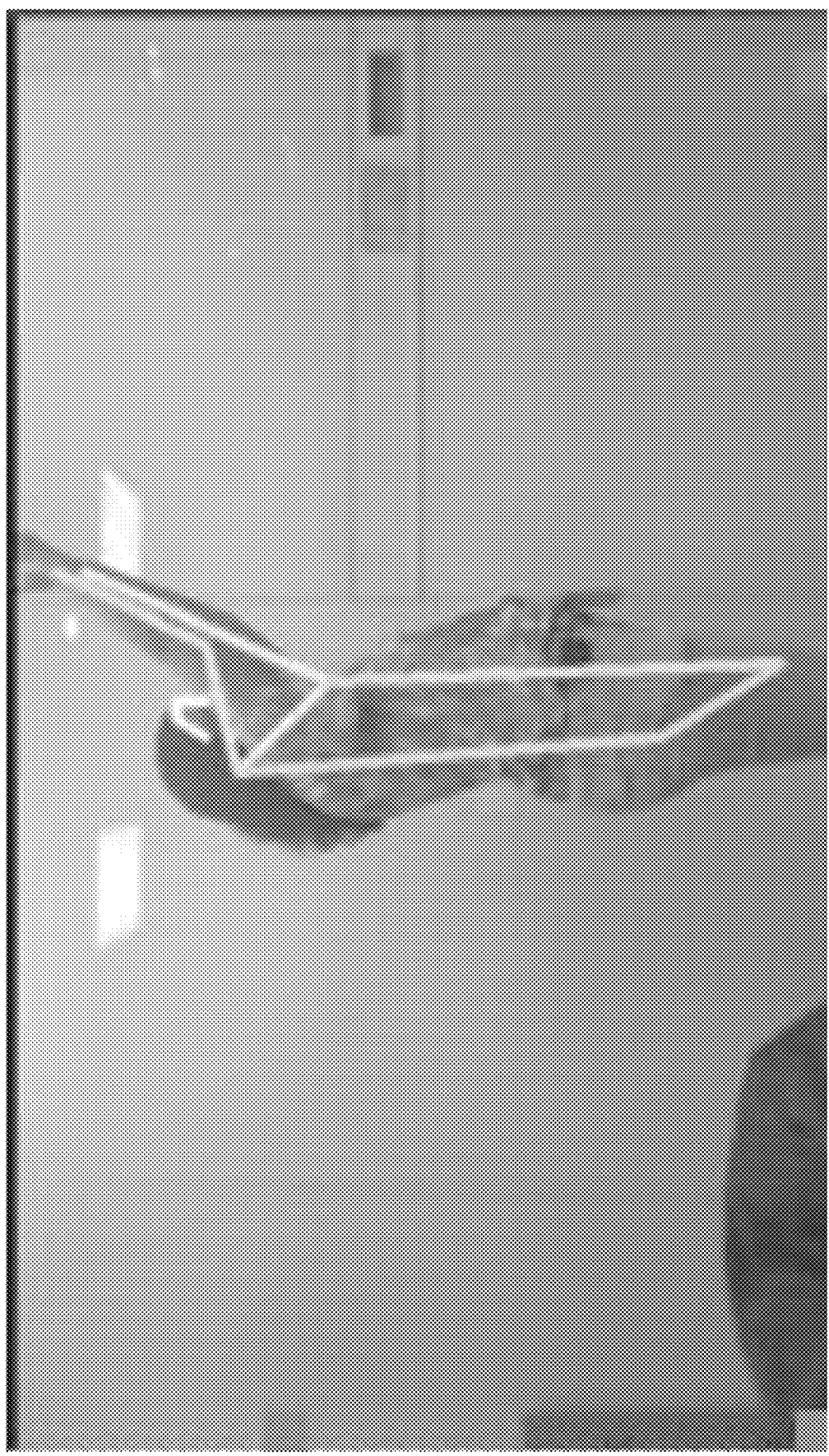

FIG. 22 illustrates an intermediate frame of the patient depicted in FIG. 21. Specifically, FIG. 22 depicts the heatmap generated by embodiments of the subject claimed innovation based on the displayed patient.

Figure 23:
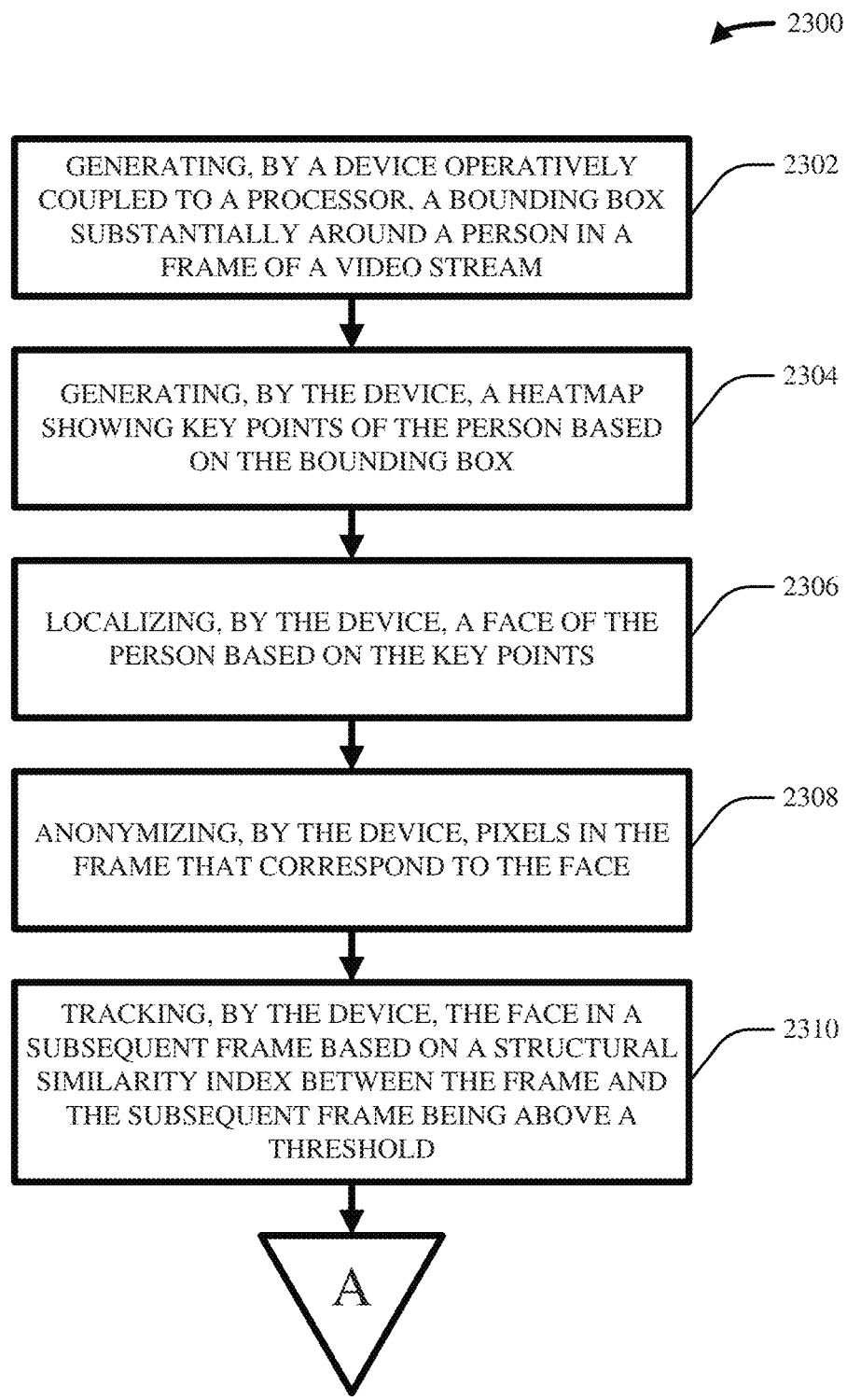
FIG. 23 illustrates a high-level flow diagram of an example, non-limiting computer-implemented method that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 23 illustrates a high-level flow diagram of an example, non-limiting computer-implemented method 2300 that can facilitate automated facial anonymization/de-identification in regular and/or occluded video streams obtained during diagnostic medical procedures in accordance with one or more embodiments described herein.

In various embodiments, act 2302 can include generating, by a device operatively coupled to a processor, a bounding box (e.g., via the bounding box component 402) substantially around a person in a frame (e.g., frame 1) of a video stream (e.g., video stream 104).

In various instances, act 2304 can include generating, by the device, a heatmap (e.g., via the heatmap component 702) showing key points or anatomical masks (e.g., primary joints and/or primary facial features) of the person based on the bounding box.

In various aspects, act 2306 can include localizing, by the device, a face or facial region of the person based on the key points or anatomical masks.

In various embodiments, act 2308 can include anonymizing, by the device, the pixels in the frame that correspond to the face or facial region (e.g., via the anonymization component 114).

In various instances, act 2310 can include tracking, by the device, the face or facial region (e.g., via the tracking component 116) in a subsequent frame (e.g., frame 2) based on a structural similarity index (e.g., computed via the SSIM component 1002) between the frame (e.g., frame 1) and the subsequent frame (e.g., frame 2) being above a threshold.

Figure 24:
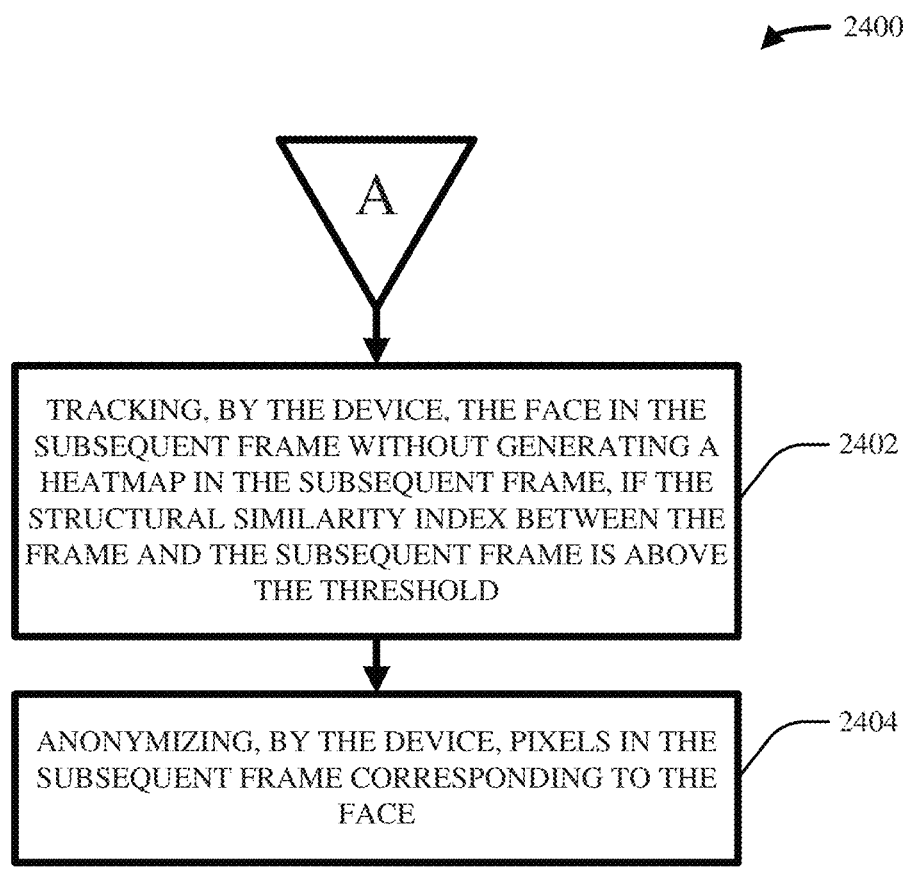
FIG. 24 illustrates a high-level flow diagram of an example, non-limiting computer-implemented method that facilitates automated facial anonymization/de-identification in regular and/or occluded video streams (e.g., RGB, RGBA8, YUYV and all supported color formats) obtained during diagnostic medical procedures in accordance with one or more embodiments described herein.

FIG. 24 illustrates a high-level flow diagram of an example, non-limiting computer-implemented method 2400 that can facilitate automated facial anonymization/de-identification in regular and/or occluded video streams obtained during diagnostic medical procedures in accordance with one or more embodiments described herein. As shown, the computer-implemented method 2400 can, in various embodiments, comprise the same components as the computer-implemented method 2300, and can further comprise acts 2402 and 2404.

In various embodiments, act 2402 can include tracking, by the device, the face or facial region (e.g., via the tracking component 116) in the subsequent frame without generating a heatmap in the subsequent frame (e.g., without running the object detection and pose estimation algorithms of the detection component 112), if the structural similarity index between the frame and the subsequent frame is above the threshold.

In various instances, act 2404 can include anonymizing, by the device, pixels in the subsequent frame corresponding to the face or facial region.

Figure 25:
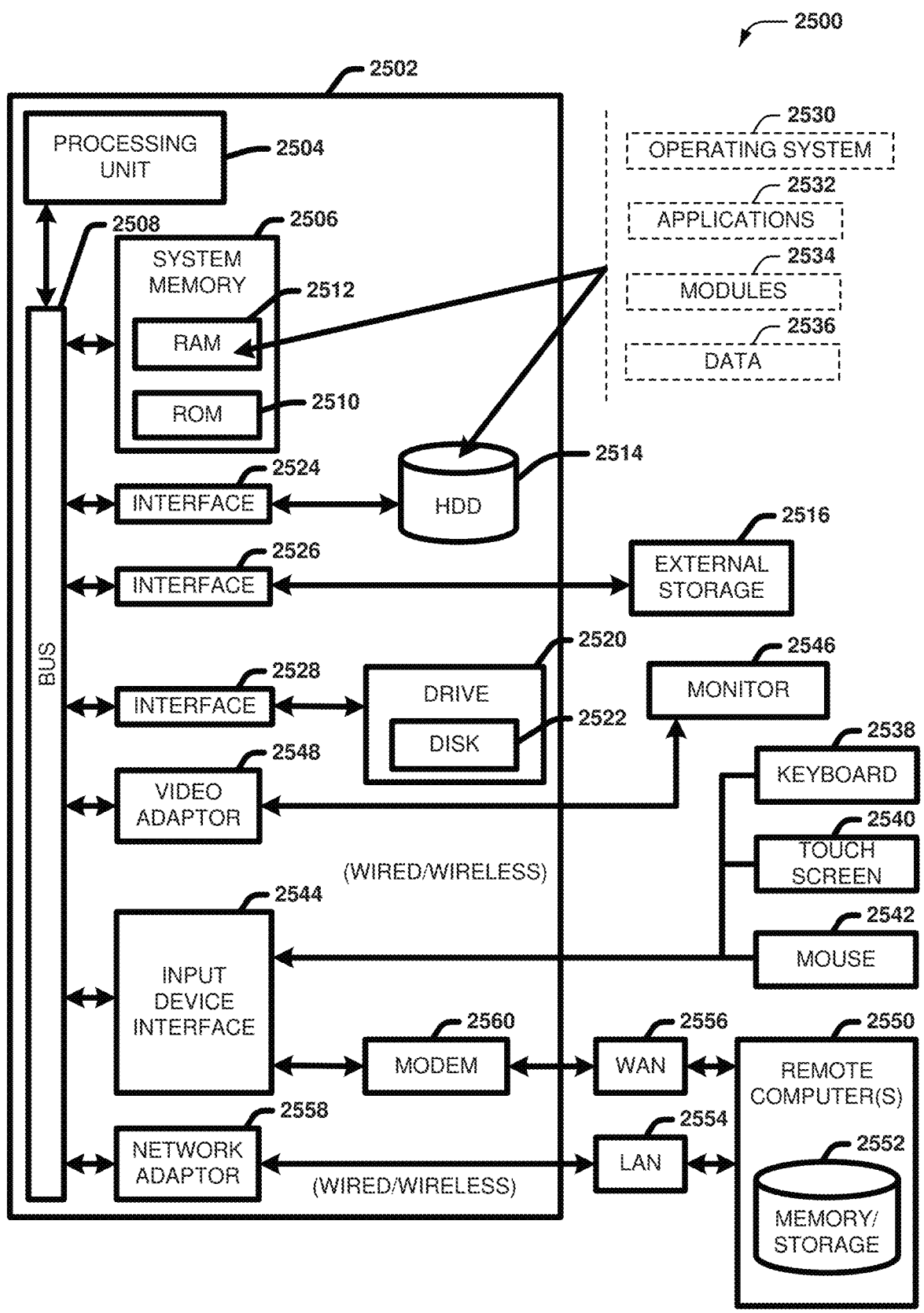
FIG. 25 illustrates a block diagram of an example, non-limiting operating environment in which one or more embodiments described herein can be facilitated.

In order to provide additional context for various embodiments described herein, FIG. 25 and the following discussion are intended to provide a brief, general description of a suitable computing environment 2500 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 25, the example environment 2500 for implementing various embodiments of the aspects described herein includes a computer 2502, the computer 2502 including a processing unit 2504, a system memory 2506 and a system bus 2508. The system bus 2508 couples system components including, but not limited to, the system memory 2506 to the processing unit 2504. The processing unit 2504 can be any of various commercially available processors. Dual microprocessors and other multi-processor architectures can also be employed as the processing unit 2504.

The system bus 2508 can be any of several types of bus structure that can further interconnect to a memory bus (with or without a memory controller), a peripheral bus, and a local bus using any of a variety of commercially available bus architectures. The system memory 2506 includes ROM 2510 and RAM 2512. A basic input/output system (BIOS) can be stored in a non-volatile memory such as ROM, erasable programmable read only memory (EPROM), EEPROM, which BIOS contains the basic routines that help to transfer information between elements within the computer 2502, such as during startup. The RAM 2512 can also include a high-speed RAM such as static RAM for caching data.

The computer 2502 further includes an internal hard disk drive (HDD) 2514 (e.g., EIDE, SATA), one or more external storage devices 2516 (e.g., a magnetic floppy disk drive (FDD) 2516, a memory stick or flash drive reader, a memory card reader, etc.) and a drive 2525, e.g., such as a solid state drive, an optical disk drive, which can read or write from a disk 2522, such as a CD-ROM disc, a DVD, a BD, etc. Alternatively, where a solid state drive is involved, disk 2522 would not be included, unless separate. While the internal HDD 2514 is illustrated as located within the computer 2502, the internal HDD 2514 can also be configured for external use in a suitable chassis (not shown). Additionally, while not shown in environment 2500, a solid state drive (SSD) could be used in addition to, or in place of, an HDD 2514. The HDD 2514, external storage device(s) 2516 and drive 2525 can be connected to the system bus 2508 by an HDD interface 2525, an external storage interface 2526 and a drive interface 2528, respectively. The interface 2525 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2502, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2512, including an operating system 2530, one or more application programs 2532, other program modules 2534 and program data 2536. All or portions of the operating system, applications, modules, and/or data can also be cached in the RAM 2512. The systems and methods described herein can be implemented utilizing various commercially available operating systems or combinations of operating systems.

Computer 2502 can optionally comprise emulation technologies. For example, a hypervisor (not shown) or other intermediary can emulate a hardware environment for operating system 2530, and the emulated hardware can optionally be different from the hardware illustrated in FIG. 25. In such an embodiment, operating system 2530 can comprise one virtual machine (VM) of multiple VMs hosted at computer 2502. Furthermore, operating system 2530 can provide runtime environments, such as the Java runtime environment or the .NET framework, for applications 2532. Runtime environments are consistent execution environments that allow applications 2532 to run on any operating system that includes the runtime environment. Similarly, operating system 2530 can support containers, and applications 2532 can be in the form of containers, which are lightweight, standalone, executable packages of software that include, e.g., code, runtime, system tools, system libraries and settings for an application.

Further, computer 2502 can be enabled with a security module, such as a trusted processing module (TPM). For instance with a TPM, boot components hash next in time boot components, and wait for a match of results to secured values, before loading a next boot component. This process can take place at any layer in the code execution stack of computer 2502, e.g., applied at the application execution level or at the operating system (OS) kernel level, thereby enabling security at any level of code execution.

A user can enter commands and information into the computer 2502 through one or more wired/wireless input devices, e.g., a keyboard 2538, a touch screen 2540, and a pointing device, such as a mouse 2542. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2504 through an input device interface 2544 that can be coupled to the system bus 2508, but can be connected by other interfaces, such as a parallel port, an IEEE 1394 serial port, a game port, a USB port, an IR interface, a BLUETOOTH® interface, etc.

A monitor 2546 or other type of display device can be also connected to the system bus 2508 via an interface, such as a video adapter 2548. In addition to the monitor 2546, a computer typically includes other peripheral output devices (not shown), such as speakers, printers, etc.

The computer 2502 can operate in a networked environment using logical connections via wired and/or wireless communications to one or more remote computers, such as a remote computer(s) 2550. The remote computer(s) 2550 can be a workstation, a server computer, a router, a personal computer, portable computer, microprocessor-based entertainment appliance, a peer device or other common network node, and typically includes many or all of the elements described relative to the computer 2502, although, for purposes of brevity, only a memory/storage device 2552 is illustrated. The logical connections depicted include wired/wireless connectivity to a local area network (LAN) 2554 and/or larger networks, e.g., a wide area network (WAN) 2556. Such LAN and WAN networking environments are commonplace in offices and companies, and facilitate enterprise-wide computer networks, such as intranets, all of which can connect to a global communications network, e.g., the Internet.

When used in a LAN networking environment, the computer 2502 can be connected to the local network 2554 through a wired and/or wireless communication network interface or adapter 2558. The adapter 2558 can facilitate wired or wireless communication to the LAN 2554, which can also include a wireless access point (AP) disposed thereon for communicating with the adapter 2558 in a wireless mode.

When used in a WAN networking environment, the computer 2502 can include a modem 2560 or can be connected to a communications server on the WAN 2556 via other means for establishing communications over the WAN 2556, such as by way of the Internet. The modem 2560, which can be internal or external and a wired or wireless device, can be connected to the system bus 2508 via the input device interface 2544. In a networked environment, program modules depicted relative to the computer 2502 or portions thereof, can be stored in the remote memory/storage device 2552. It will be appreciated that the network connections shown are example and other means of establishing a communications link between the computers can be used.

When used in either a LAN or WAN networking environment, the computer 2502 can access cloud storage systems or other network-based storage systems in addition to, or in place of, external storage devices 2516 as described above, such as but not limited to a network virtual machine providing one or more aspects of storage or processing of information. Generally, a connection between the computer

2502 and a cloud storage system can be established over a LAN 2554 or WAN 2556 e.g., by the adapter 2558 or modem 2560, respectively. Upon connecting the computer 2502 to an associated cloud storage system, the external storage interface 2526 can, with the aid of the adapter 2558 and/or modem 2560, manage storage provided by the cloud storage system as it would other types of external storage. For instance, the external storage interface 2526 can be configured to provide access to cloud storage sources as if those sources were physically connected to the computer 2502.

The computer 2502 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject claimed innovation are provided in the subject matter that follows:

1. A system, comprising: a memory that stores computer-executable components; and a processor, operably coupled to the memory, that executes the computer-executable components stored in the memory, wherein the computer-executable components comprise: a detection component that generates a bounding box substantially around a person in a frame of a video stream, generates a heatmap showing key points or anatomical masks of the person based on the bounding box, and localizes a face or facial region of the person based on the key points or anatomical masks; an anonymization component that anonymizes pixels in the frame that correspond to the face or facial region; and a tracking component that tracks the face or facial region in a subsequent frame based on a structural similarity index between the frame and the subsequent frame being above a threshold.

2. The system of any preceding clause wherein if the structural similarity index between the frame and the subsequent frame is above the threshold, the tracking component tracks the face or facial region in the subsequent frame, the detection component does not generate a bounding box or a heatmap in the subsequent frame, and the anonymization component anonymizes pixels in the subsequent frame corresponding to the face or facial region.

3. The system of any preceding clause wherein the threshold is 80% and a frame rate of the video stream is 30 frames per second.

4. The system of any preceding clause wherein: the detection component employs a first machine learning algorithm to generate the bounding box; the detection component employs a second machine learning algorithm to generate the heatmap and to localize the face or facial region; and the tracking component employs a third machine learning algorithm to track the face or facial region.

5. The system of any preceding clause wherein: the first machine learning algorithm comprises a trained YOLOv3 object detection algorithm; the second machine learning algorithm comprises a trained Simple Pose ResNet algorithm; and the third machine learning algorithm comprises a trained median flow tracker.

6. The system of any preceding clause wherein the anonymization component anonymizes pixels via pixilation or gaussian blurring.

7. The system of any preceding clause wherein the detection component upscales the bounding box to ensure that a substantial portion of the person is within the bounding box.

8. A computer-implemented method, comprising: generating, by a device operatively coupled to a processor, a bounding box substantially around a person in a frame of a video stream; generating, by the device, a heatmap showing key points or anatomical masks of the person based on the bounding box; localizing, by the device, a face or facial region of the person based on the key points or anatomical masks; anonymizing, by the device, pixels in the frame that correspond to the face or facial region; and tracking, by the device, the face or facial region in a subsequent frame based on a structural similarity index between the frame and the subsequent frame being above a threshold.

9. The computer-implemented method of any preceding clause further comprising: tracking, by the device, the face or facial region in the subsequent frame without generating a heatmap in the subsequent frame, if the structural similarity index between the frame and the subsequent frame is above the threshold; and anonymizing, by the device, pixels in the subsequent frame corresponding to the face or facial region.

10. The computer-implemented method of any preceding clause wherein the threshold is 80% and a frame rate of the video stream is 30 frames per second.

11. The computer-implemented method of any preceding clause wherein: the generating the bounding box employs a first machine learning algorithm; the generating the heatmap and localizing the face or facial region employs a second machine learning algorithm; and the tracking the face or facial region employs a third machine learning algorithm.

12. The computer-implemented method of any preceding clause wherein: the first machine learning algorithm comprises a trained YOLOv3 object detection algorithm; the second machine learning algorithm comprises a trained Simple Pose ResNet algorithm; and the third machine learning algorithm comprises a trained median flow tracker.

13. The computer-implemented method of any preceding clause wherein the anonymizing pixels employs pixilation or gaussian blurring.

14. The computer-implemented method of any preceding clause further comprising: upscaling, by the device, the bounding box to ensure that a substantial portion of the person is within the bounding box.

15. A computer program product for facilitating automated face or facial region anonymization in video streams, the computer program product comprising a computer readable memory having program instructions embodied therewith, the program instructions executable by a processing component to cause the processing component to: generate a bounding box substantially around a person in a frame of a video stream; generate a heatmap showing key points or anatomical masks of the person based on the bounding box; localize a face or facial region of the person based on the key points or anatomical masks; anonymize pixels in the frame that correspond to the face or facial region; and track the face or facial region in a subsequent frame based on a structural similarity index between the frame and the subsequent frame being above a threshold.

16. The computer program product of any preceding clause wherein the program instructions are further executable to cause the processing component to: track the face or facial region in the subsequent frame without generating a heatmap in the subsequent frame, if the structural similarity index between the frame and the subsequent frame is above the threshold; and anonymize pixels in the subsequent frame corresponding to the face or facial region.

17. The computer program product of any preceding clause wherein the threshold is 80% and a frame rate of the video stream is 30 frames per second.

18. The computer program product of any preceding clause wherein: the processing component generates the bounding box via a first machine learning algorithm; the processing component generates the heatmap and localizes the face or facial region via a second machine learning algorithm; and the processing component tracks the face or facial region via a third machine learning algorithm.

19. The computer program product of any preceding clause wherein: the first machine learning algorithm comprises a trained YOLOv3 object detection algorithm; the second machine learning algorithm comprises a trained Simple Pose ResNet algorithm; and the third machine learning algorithm comprises a trained median flow tracker.

20. The computer program product of any preceding clause wherein the program instructions are further executable to cause the processing component to: upscale the bounding box to ensure that a substantial portion of the person is within the bounding box.

What is claimed is:

1. A system, comprising:
a memory that stores computer-executable components; and
a processor, operably coupled to the memory, that executes the computer-executable components stored in the memory, wherein the computer-executable components comprise:
a detection component that generates a bounding box substantially around a person in a frame of a video stream, generates a heatmap showing key points or anatomical masks of the person based on the bounding box, and localizes a face or facial region of the person based on the key points or anatomical masks;
an anonymization component that anonymizes pixels in the frame that correspond to the face or facial region; and
a tracking component that tracks the face or facial region in a subsequent frame based on a structural similarity index between the frame and the subsequent frame being above a threshold.

2. The system of claim 1, wherein:
if the structural similarity index between the frame and the subsequent frame is above the threshold, the tracking component tracks the face or facial region in the subsequent frame, the detection component does not generate a bounding box or a heatmap in the subsequent frame, and the anonymization component anonymizes pixels in the subsequent frame corresponding to the face or facial region.

3. The system of claim 2, wherein the threshold is 80% and a frame rate of the video stream is 30 frames per second.

4. The system of claim 1, wherein:
the detection component employs a first machine learning algorithm to generate the bounding box;
the detection component employs a second machine learning algorithm to generate the heatmap and to localize the face or facial region; and
the tracking component employs a third machine learning algorithm to track the face or facial region.

5. The system of claim 4, wherein:
the first machine learning algorithm comprises a trained YOLOv3 object detection algorithm;
the second machine learning algorithm comprises a trained Simple Pose ResNet algorithm; and
the third machine learning algorithm comprises a trained median flow tracker.

6. The system of claim 1, wherein the anonymization component anonymizes pixels via pixilation or gaussian blurring.

7. The system of claim 1, wherein the detection component upscales the bounding box to ensure that a substantial portion of the person is within the bounding box.

8. A computer-implemented method, comprising:
generating, by a device operatively coupled to a processor, a bounding box substantially around a person in a frame of a video stream;
generating, by the device, a heatmap showing key points or anatomical masks of the person based on the bounding box;
localizing, by the device, a face or facial region of the person based on the key points or anatomical masks;
anonymizing, by the device, pixels in the frame that correspond to the face or facial region; and
tracking, by the device, the face or facial region in a subsequent frame based on a structural similarity index between the frame and the subsequent frame being above a threshold.

9. The computer-implemented method of claim 8, further comprising:
tracking, by the device, the face or facial region in the subsequent frame without generating a heatmap in the subsequent frame, if the structural similarity index between the frame and the subsequent frame is above the threshold; and
anonymizing, by the device, pixels in the subsequent frame corresponding to the face or facial region.

10. The computer-implemented method of claim 9, wherein the threshold is 80% and a frame rate of the video stream is 30 frames per second.

11. The computer-implemented method of claim 8, wherein:
the generating the bounding box employs a first machine learning algorithm;
the generating the heatmap and localizing the face or facial region employs a second machine learning algorithm; and
the tracking the face or facial region employs a third machine learning algorithm.

12. The computer-implemented method of claim 11, wherein:
the first machine learning algorithm comprises a trained YOLOv3 object detection algorithm;
the second machine learning algorithm comprises a trained Simple Pose ResNet algorithm; and
the third machine learning algorithm comprises a trained median flow tracker.

13. The computer-implemented method of claim 8, wherein the anonymizing pixels employs pixilation or gaussian blurring.

14. The computer-implemented method of claim 8, further comprising:
   upscaling, by the device, the bounding box to ensure that a substantial portion of the person is within the bounding box.

15. A computer program product for facilitating automated face or facial region anonymization in video streams, the computer program product comprising a computer readable memory having program instructions embodied therewith, the program instructions executable by a processing component to cause the processing component to:
   generate a bounding box substantially around a person in a frame of a video stream;
   generate a heatmap showing key points or anatomical masks of the person based on the bounding box;
   localize a face or facial region of the person based on the key points or anatomical masks;
   anonymize pixels in the frame that correspond to the face or facial region; and
   track the face or facial region in a subsequent frame based on a structural similarity index between the frame and the subsequent frame being above a threshold.

16. The computer program product of claim 15, wherein the program instructions are further executable to cause the processing component to:
   track the face or facial region in the subsequent frame without generating a heatmap in the subsequent frame, if the structural similarity index between the frame and the subsequent frame is above the threshold; and
   anonymize pixels in the subsequent frame corresponding to the face or facial region.

17. The computer program product of claim 16, wherein the threshold is 80% and a frame rate of the video stream is 30 frames per second.

18. The computer program product of claim 15, wherein:
   the processing component generates the bounding box via a first machine learning algorithm;
   the processing component generates the heatmap and localizes the face or facial region via a second machine learning algorithm; and
   the processing component tracks the face or facial region via a third machine learning algorithm.

19. The computer program product of claim 18, wherein:
   the first machine learning algorithm comprises a trained YOLOv3 object detection algorithm;
   the second machine learning algorithm comprises a trained Simple Pose ResNet algorithm; and
   the third machine learning algorithm comprises a trained median flow tracker.

20. The computer program product of claim 15, wherein the program instructions are further executable to cause the processing component to:
   upscale the bounding box to ensure that a substantial portion of the person is within the bounding box.

\* \* \* \* \*